(12) United States Patent
Margaron et al.

(10) Patent No.: US 8,313,763 B2
(45) Date of Patent: Nov. 20, 2012

(54) SUSTAINED DELIVERY FORMULATIONS OF RAPAMYCIN COMPOUNDS

(75) Inventors: Philippe Maria Clotaire Margaron, Vancouver (CA); Eric Dadey, Fort Collins, CO (US); Christopher M. Lindemann, Loveland, CO (US); Ruihong Li, Vancouver (CA)

(73) Assignee: Tolmar Therapeutics, Inc., Fort Collins, CO (US)

( * ) Notice: Subject to any disclaimer, the term of this patent is extended or adjusted under 35 U.S.C. 154(b) by 1227 days.

(21) Appl. No.: 11/706,569

(22) Filed: Feb. 15, 2007

(65) Prior Publication Data

US 2007/0280992 A1 Dec. 6, 2007

Related U.S. Application Data

(63) Continuation-in-part of application No. 11/244,438, filed on Oct. 4, 2005.

(60) Provisional application No. 60/615,727, filed on Oct. 4, 2004, provisional application No. 60/628,630, filed on Nov. 17, 2004, provisional application No. 60/629,133, filed on Nov. 18, 2004.

(51) Int. Cl.
*A61F 2/00* (2006.01)
(52) U.S. Cl. ....................................................... 424/427
(58) Field of Classification Search .................. None
See application file for complete search history.

(56) References Cited

U.S. PATENT DOCUMENTS

| | | |
|---|---|---|
| 3,416,530 A | 12/1968 | Ness |
| 3,963,025 A | 6/1976 | Whitaker et al. |
| 3,993,749 A | 11/1976 | Sehgal et al. |
| 4,053,580 A | 10/1977 | Chien et al. |
| 4,164,559 A | 8/1979 | Miyata et al. |
| 4,179,497 A | 12/1979 | Cohen et al. |
| 4,249,531 A | 2/1981 | Heller et al. |
| 4,316,885 A | 2/1982 | Rakhit |
| 4,346,709 A | 8/1982 | Schmitt |
| 4,401,653 A | 8/1983 | Eng |
| 4,612,302 A | 9/1986 | Szabo et al. |
| 4,652,441 A | 3/1987 | Okada et al. |
| 4,684,620 A | 8/1987 | Hruby et al. |
| 4,853,371 A | 8/1989 | Coy et al. |
| 4,885,171 A | 12/1989 | Surrendra et al. |
| 4,917,893 A | 4/1990 | Okada et al. |

(Continued)

FOREIGN PATENT DOCUMENTS

WO WO-2004/027027 A1 4/2004

(Continued)

OTHER PUBLICATIONS

"U.S. Appl. No. 11/244,438, Response filed Jul. 8, 2009 to Non-Final Office Action mailed Jan. 8, 2009", 27 pgs.

(Continued)

*Primary Examiner* — Paul Dickinson
(74) *Attorney, Agent, or Firm* — Schwegman, Lundberg & Woessner, P.A.

(57) ABSTRACT

The present invention relates to a rapamycin sustained release delivery system for treatment of diseases responsive to rapamycin. The sustained release delivery system of the invention includes a flowable composition containing rapamycin or a rapamycin derivative, which is capable of providing an implant containing the rapamycin or derivative thereof. The flowable composition may be injected into tissue whereupon it coagulates to become the solid or gel, monolithic implant. The flowable composition includes a biodegradable, thermoplastic polymer, an organic liquid and rapamycin or a rapamycin derivative.

19 Claims, 10 Drawing Sheets

U.S. PATENT DOCUMENTS

| | | | |
|---|---|---|---|
| 4,938,763 A | 7/1990 | Dunn et al. |
| 4,954,298 A | 9/1990 | Yamamoto et al. |
| 5,061,492 A | 10/1991 | Okada et al. |
| 5,078,999 A | 1/1992 | Warner et al. |
| 5,080,899 A | 1/1992 | Sturm et al. |
| 5,100,883 A | 3/1992 | Schiehser |
| 5,100,899 A | 3/1992 | Calne |
| 5,102,876 A | 4/1992 | Caufield |
| 5,118,677 A | 6/1992 | Caufield |
| 5,120,842 A | 6/1992 | Failli et al. |
| 5,130,307 A | 7/1992 | Failli et al. |
| 5,138,051 A | 8/1992 | Hughes et al. |
| 5,151,413 A | 9/1992 | Caufield et al. |
| 5,164,399 A | 11/1992 | Failli et al. |
| 5,206,018 A | 4/1993 | Sehgal et al. |
| 5,233,036 A | 8/1993 | Hughes |
| 5,278,201 A | 1/1994 | Dunn et al. |
| 5,278,202 A | 1/1994 | Dunn et al. |
| 5,283,236 A | 2/1994 | Chiou |
| 5,288,711 A | 2/1994 | Mitchell et al. |
| 5,310,903 A | 5/1994 | Goulet et al. |
| 5,321,009 A | 6/1994 | Baeder et al. |
| 5,324,519 A | 6/1994 | Dunn et al. |
| 5,330,767 A | 7/1994 | Yamamoto et al. |
| 5,340,849 A | 8/1994 | Dunn et al. |
| 5,344,833 A | 9/1994 | Hughes |
| 5,346,893 A | 9/1994 | Failli et al. |
| 5,362,718 A | 11/1994 | Skotnicki et al. |
| 5,387,589 A | 2/1995 | Kulkarni |
| 5,446,048 A | 8/1995 | Failli et al. |
| 5,476,663 A | 12/1995 | Okada et al. |
| 5,480,656 A | 1/1996 | Okada et al. |
| 5,487,897 A | 1/1996 | Polson et al. |
| 5,504,091 A | 4/1996 | Molnar-Kimber et al. |
| 5,561,138 A | 10/1996 | Armstrong |
| 5,567,709 A | 10/1996 | Skotnicki et al. |
| 5,575,987 A | 11/1996 | Kamei et al. |
| 5,599,552 A | 2/1997 | Dunn et al. |
| 5,631,020 A | 5/1997 | Okada et al. |
| 5,631,021 A | 5/1997 | Okada et al. |
| 5,637,590 A | 6/1997 | Skotnicki et al. |
| 5,643,607 A | 7/1997 | Okada et al. |
| 5,651,990 A | 7/1997 | Takada et al. |
| 5,681,873 A | 10/1997 | Norton et al. |
| 5,702,716 A | 12/1997 | Dunn et al. |
| 5,718,922 A | 2/1998 | Herrero et al. |
| 5,733,950 A | 3/1998 | Dunn et al. |
| 5,736,152 A | 4/1998 | Dunn |
| 5,739,176 A | 4/1998 | Dunn et al. |
| 5,744,153 A | 4/1998 | Yewey et al. |
| 5,759,563 A | 6/1998 | Yewey et al. |
| 5,780,044 A | 7/1998 | Yewey et al. |
| 5,792,469 A | 8/1998 | Tipton et al. |
| 5,863,985 A | 1/1999 | Shalaby et al. |
| 5,922,730 A | 7/1999 | Hu et al. |
| 5,945,115 A | 8/1999 | Dunn et al. |
| 5,955,457 A | 9/1999 | Lee et al. |
| 5,990,194 A | 11/1999 | Dunn et al. |
| 6,113,943 A | 9/2000 | Okada et al. |
| 6,121,329 A | 9/2000 | Fujii et al. |
| 6,143,314 A | 11/2000 | Chandrashekar et al. |
| 6,221,958 B1 | 4/2001 | Shalaby et al. |
| 6,261,583 B1 | 7/2001 | Dunn et al. |
| 6,264,971 B1 | 7/2001 | Darougar et al. |
| 6,331,313 B1 | 12/2001 | Wong et al. |
| 6,342,250 B1 | 1/2002 | Masters |
| 6,355,657 B1 | 3/2002 | Osborne |
| 6,372,245 B1 | 4/2002 | Bowman et al. |
| 6,395,293 B2 | 5/2002 | Polson et al. |
| 6,399,625 B1 | 6/2002 | Zhu |
| 6,440,990 B1 | 8/2002 | Cottens et al. |
| 6,461,631 B1 | 10/2002 | Dunn et al. |
| RE37,950 E | 12/2002 | Dunn et al. |
| 6,528,080 B2 | 3/2003 | Dunn et al. |
| 6,565,874 B1 | 5/2003 | Dunn et al. |
| 6,670,355 B2 | 12/2003 | Azrolan et al. |
| 6,677,357 B2 | 1/2004 | Zhu et al. |
| 6,680,330 B2 | 1/2004 | Zhu et al. |
| 2004/0010224 A1 | 1/2004 | Bodmeier |
| 2004/0022859 A1 | 2/2004 | Chen et al. |
| 2004/0170665 A1 | 9/2004 | Donovan |
| 2005/0064010 A1* | 3/2005 | Cooper et al. ............... 424/423 |
| 2005/0187241 A1 | 8/2005 | Wen et al. |
| 2006/0210604 A1 | 9/2006 | Dadey et al. |

FOREIGN PATENT DOCUMENTS

| | | |
|---|---|---|
| WO | WO-2005/011813 A2 | 2/2005 |
| WO | WO-2005/110473 A2 | 11/2005 |
| WO | WO-2006/086888 A1 | 8/2006 |
| WO | WO-2008/100532 A1 | 8/2008 |
| WO | WO-2008/100576 A2 | 8/2008 |

OTHER PUBLICATIONS

"U.S. Appl. No. 11/244,438, Response filed Nov. 25, 2009 to Restriction Requirement mailed Oct. 29, 2009", 19 pgs.

"U.S. Appl. No. 11/244,438, Restriction Requirement mailed Oct. 29, 2009", 6 pgs.

"European Application Serial No. 08725587.3, Communication mailed Oct. 5, 2009", 2 pgs.

"European Application Serial No. 08725587.3, Response filed Nov. 4, 2009 to Communication mailed Oct. 5, 2009", 11 pgs.

"U.S. Appl. No. 11/244,438 Final Office Action mailed Oct. 4, 2010".

"U.S. Appl. No. 11/244,438, Non-Final Office Action mailed Apr. 1, 2010", 9 pgs.

"U.S. Appl. No. 11/244,438, Response filed Aug. 2, 2010, to Non Final Office Action mailed Apr. 1, 2010", 19 pgs.

Chou, T. C., et al., "Quantitative Analysis of Dose-Effect Relationships: The Combined Effects of Multiple Drugs or Enzyme Inhibitors", *Adv. Enzyme Regul.*, 22, (1984), 27-55.

Janus, A., et al., "The Mammalian Target of the Rapamycin (mTOR) Kinase Pathway: Its Role in Tumourigeneis and Targeted Antitumour Therapy", *Cellular & Molecular Biology Letters*, 10(3), (2005), 479-498.

Jungbauer, F. H., et al., "Toxic hygroscopic contact reaction to N-Methyl-2-Pyrrolidone", *Contact Dermatitis*, 45(5), (Nov. 2001), 303-304.

Leira, H. L., et al., "Irritant Cutaneous Reactions to N-Methyl-2-Pyrrolidone (NMP)", *Contact Dermatitis*, 27(3), (1992), 148-150.

"U.S. Appl. No. 11/244,438, Non-Final Office Action mailed Jan. 8, 2009", 15 pgs.

"U.S. Appl. No. 11/244,438, Restriction Requirement mailed Sep. 30, 2008", 10 pgs.

"U.S. Appl. No. 11/244,438, Response filed Oct. 14, 2008 to Restriction Requirement mailed Sep. 30, 2008", 22 pgs.

"International Application Serial No. PCT/US2008/001974, International Search Report mailed Jun. 3, 2009", 4 pgs.

"International Application Serial No. PCT/US2008/001974, Written Opinion mailed Jun. 3, 2009", 11 pgs.

"Canadian Application Serial No. 2,678,176, Office Action mailed Aug. 3, 2011", 2 pgs.

"European Office Action Jan. 18, 2012".

"Canadian Application Serial No. 2,678,176, Response filed Feb. 3, 2012 to Office Action mailed Aug. 3, 2011", 20 pgs.

Dejneka, N. S., et al., "Systemic rapamycin inhibits retinal and choroidal neovascularization in mice", *Molecular Vision*, 10, (Dec. 22, 2004), 964-972.

Urtti, A., "Challenges and obstacles of ocular pharmacokinetics and drug delivery", *Advanced Drug Delivery Reviews*, 58, (2006), 1131-1135.

\* cited by examiner

Subcutaneous Evaluation: Injection Volume

Comparison of the Release of Rapamycin from ATRIGEL Following a 10 or 100uL Subcutaneous Injection in Male Rats Rapamycin distribution in the rabbit vitreous A — 5% Rapamycin 95% of [50% 65/35 PLGH 0.26 InV and 50% NMP] – Total amount delivered 0.5mg
B — 10% Rapamycin 90% of [50% 65/35 PLGH 0.26 InV and 50% NMP] - Total amount delivered 1mg
C — 10% Rapamycin 90% of [50% 75/25 PLGH 13 kDa and 50% NMP] - Total amount delivered 1mg 7-Day Release Comparison of Subcutaneous, Intravitreal and Sub-Tenon's Injection Routes Angiographical evaluation of the effect of rapamycin on the development of CNV in the laser-induced CNV model in rat. N = non-leaky CNV lesion; L = leaky CNV lesion; P = partial leaky CNV lesion.

Effect of rapamycin on the CNV area and CD31-positive cell count within the CNV area in the laser-induced CNV model.

Effects of intravitreally administered rapamycin on serine phosphorylation of S6 ribosomal protein extracted from chorioretinal tissues at Days 1, 3 and 7 post-dosing.

SUSTAINED DELIVERY FORMULATIONS OF RAPAMYCIN COMPOUNDS

CROSS-REFERENCE TO RELATED APPLICATIONS

This application is a continuation-in-part of U.S. patent application Ser. No. 11/244,438, filed Oct. 4, 2005, which claims the benefit of priority to U.S. Provisional Patent Application Ser. Nos. 60/615,727 (filed Oct. 4, 2004), 60/628,630 (filed Nov. 17, 2004), and 60/629,133 (filed Nov. 18, 2004). Each of these applications is incorporated herein by reference.

FIELD OF THE INVENTION

The present invention relates to a rapamycin sustained release delivery system for treatment of diseases ameliorated by rapamycin and its derivatives. The sustained release delivery system of the invention includes a flowable composition containing rapamycin, and an implant containing the rapamycin.

BACKGROUND OF THE INVENTION

Rapamycin (also known as sirolimus and marketed under the trade name Rapamune®) is a known macrolide with potent immunosuppressive properties. It also possesses anti-fungal, anti-tumor and anti-inflammatory properties. Rapamycin binds to a member of the FK binding protein (FKBP) family. The rapamycin/FKBP complex binds to the protein kinase mTOR. This binding to mTOR blocks activation of signal transduction pathways and causes arrest of the cell cycle in the G1 phase.

The mTOR signaling network plays a central role in cell survival and proliferation. The network includes multiple players, including PTEN, LKB1, TSC1, TSC2, PI3K, Akt, and eIF4E, among others. Rapamycin is thus an ideal agent for targeting many conditions characterized by detrimental cell survival and proliferation.

There is a continuing need to develop products providing increased bioavailability of rapamycin and rapamycin derivatives. In particular, there is a need to develop sustained release formulations of rapamycin and rapamycin derivatives that do not suffer from low bioavailability, poor release kinetics, injection site toxicity, relatively large volume injections and inconveniently short duration of release. This need is especially evident when treating the sensitive tissues of the eye.

SUMMARY OF THE INVENTION

The present invention is directed to a rapamycin sustained release delivery system capable of delivering rapamycin and its derivatives for a duration of about 1 week to about 12 months or even longer. The rapamycin sustained release delivery system includes a flowable composition that can provide a gel or solid implant for the sustained release of rapamycin. The implant is produced from the flowable composition. In certain preferred embodiments, the rapamycin sustained release delivery system provides in situ 1-month and 6-month release profiles characterized by high bioavailability and minimal risk of permanent tissue damage and low risk of tissue necrosis.

The present invention is directed to a rapamycin sustained release delivery system. This delivery system includes a flowable composition that can provide a controlled, sustained release implant. The flowable composition of the invention includes a biodegradable thermoplastic polymer, a biocompatible, polar, aprotic organic liquid and rapamycin or a rapamycin derivative. The flowable composition of the invention may be transformed into the implant of the invention by contact with water, body fluid or other aqueous medium. In one embodiment, the flowable composition is injected into the body whereupon it transforms in situ into the solid or gel implant of the invention.

The thermoplastic polymer of the flowable composition and implant is at least substantially insoluble in an aqueous medium or body fluid, preferably, essentially completely insoluble in those media. The thermoplastic polymer may be a homopolymer, a copolymer or a terpolymer of repeating monomeric units linked by such groups as ester groups, anhydride groups, carbonate groups, amide groups, urethane groups, urea groups, ether groups, esteramide groups, acetal groups, ketal groups, orthocarbonate groups and any other organic functional group that can be hydrolyzed by enzymatic or hydrolytic reaction (i.e., is biodegradable by this hydrolytic action). The preferred thermoplastic polymer, polyester, may be composed of units of one or more hydroxycarboxylic acid residues or diol and dicarboxylic acid residues, wherein the distribution of differing residues may be random, block, paired or sequential.

When the biodegradable thermoplastic polymer is a polyester, the preferable polyesters include a polylactide, a polyglycolide, a polycaprolactone, a copolymer thereof, a terpolymer thereof, or any combination thereof, optionally incorporating a third mono-alcohol or polyol component. More preferably, the biodegradable thermoplastic polyester is a polylactide, a polyglycolide, a copolymer thereof, a terpolymer thereof, or a combination thereof, optionally incorporating a third mono-alcohol or polyol component. More preferably, the suitable biodegradable thermoplastic polyester is 65/35 poly(lactide-co-glycolide) having a carboxy terminal group or is a 75/25, 65/35, 50/50 or an 85/15 PLG with a carboxy terminal group (hereinafter PLGH) or such a PLG formulated with one or more mono-alcohol or polyol units (hereinafter PLG). When a mono-alcohol or polyol is incorporated into the polyester, the mono-alcohol or polyol constitutes a third covalent component of the polymer chain. When a mono-alcohol is incorporated, the carboxy terminus of the polyester is esterified with the mono-alcohol. When a polyol is incorporated, it chain extends and optionally branches the polyester such that the termini of the polyester are all alcohol groups. The polyol functions as a polyester polymerization point with the polyester chains extending from multiple hydroxyl moieties of the polyol, and those hydroxyl moieties are esterified by a carboxyl group of the polyester chain. For an embodiment employing a diol, the polyester is linear with polyester chains extending from both esterified hydroxy groups. For an embodiment employing a triol or higher polyol, the polyester may be linear or may be branched with polyester chains extending from the esterified hydroxy groups. Examples of polyols include aliphatic and aromatic diols, saccharides such as glucose, lactose, maltose, sorbitol, triols such as glycerol, fatty alcohols and the like, tetraols, pentaols, hexaols and the like.

The biodegradable thermoplastic polymer can be present in any suitable amount, provided the biodegradable thermoplastic polymer is at least substantially insoluble in aqueous medium or body fluid. The biodegradable thermoplastic polymer is present in about 10 wt. % to about 95 wt. % of the flowable composition, preferably present in about 20 wt. % to about 70 wt. % of the flowable composition or more preferably is present in about 30 wt. % to about 60 wt. % of the flowable composition. Preferably, the biodegradable thermoplastic polymer has an average molecular weight of about 5,000 to about 75,000 or more preferably about 10,000 to about 35,000.

The flowable composition of the invention also includes a biocompatible, polar aprotic organic liquid. The biocompatible polar aprotic liquid can be an amide, an ester, a carbonate, a ketone, an ether, a sulfonyl or any other organic compound that is liquid at ambient temperature, is polar and is aprotic. The biocompatible polar aprotic organic liquid may be only very slightly soluble to completely soluble in all proportions in body fluid. While the organic liquid generally will have similar solubility profiles in aqueous medium and body fluid, body fluid is typically more lipophilic than aqueous medium. Consequently, some organic liquids that are insoluble in aqueous medium will be at least slightly soluble in body fluid. These examples of organic liquid are included within the definition of organic liquids according to the invention.

Preferably, the biocompatible polar aprotic liquid is N-methyl-2-pyrrolidone, 2-pyrrolidone, N,N-dimethylformamide, dimethyl sulfoxide, propylene carbonate, caprolactam, triacetin, or any combination thereof. More preferably, the biocompatible polar aprotic liquid is N-methyl-2-pyrrolidone. Preferably, the polar aprotic organic liquid is present in about 30 wt. % to about 80 wt. % of the composition or is present in about 40 wt. % to about 60 wt. % of the composition.

The flowable composition of the invention also includes rapamycin and rapamycin derivatives which are oligopeptides. The rapamycin is present in at least about a 0.01 wt. % concentration in the flowable composition with the upper limit being the limit of dispersibility of the peptide within the flowable composition. Preferably, the concentration is about 0.5 wt. % to about 30 wt. % of the flowable composition or more preferably about 1 wt. % to about 15 wt. % of the flowable composition.

When prepared for local administration to the eye or the ocular region, the flowable composition of the invention may include total dosage of rapamycin in the range of 0.01 mg to 10 mg, preferably in the range of 0.10 mg to 5 mg, and more preferably in the range of 0.5 mg to 2.5 mg.

Preferably, the flowable composition as described herein is formulated as an injectable delivery system. The flowable composition preferably has a volume of about 0.001 mL to about 1 mL, or preferably has a volume of about 0.01 mL to about 0.20 mL. The injectable composition is preferably formulated for administration about once per week, about once per month, about once per three months, about once per four months, about once per six months, about once per nine months to about 12 months or even less frequently. Preferably, the flowable composition is a liquid or a gel composition, suitable for injection into a patient.

Excipients, release modifiers, plasticizers, pore forming agents, gelation liquids, non-active extenders, and other ingredients may also be included within the rapamycin sustained release delivery system of the invention. Upon administration of the flowable composition, some of these additional ingredients, such as gelation liquids and release modifiers will remain with the implant, while others, such as pore forming agents will separately disperse and/or diffuse along with the organic liquid.

The present invention also is directed to a method for forming a flowable composition. The method includes mixing, in any order, a biodegradable thermoplastic polymer, a biocompatible polar aprotic liquid, and rapamycin or any rapamycin derivative. These ingredients, their properties, and preferred amounts are as disclosed above. The mixing is performed for a sufficient period of time effective to form the flowable composition for use as a controlled release implant.

Preferably, the biocompatible thermoplastic polymer and the biocompatible polar aprotic organic liquid are mixed together to form a mixture and the mixture is then combined with the rapamycin to form the flowable composition. Preferably, the flowable composition is a solution or dispersion, especially preferably a solution, of the rapamycin or rapamycin derivative and biodegradable thermoplastic polymer in the organic liquid. The flowable composition preferably includes an effective amount of a biodegradable thermoplastic polymer, an effective amount of a biocompatible polar aprotic organic liquid and an effective amount of rapamycin. These ingredients, the preferred ingredients, their properties, and preferred amounts are as disclosed above.

The present invention also is directed to a method of forming a biodegradable implant in situ, in a living patient. The method includes injecting the flowable composition described herein within the body of a patient and allowing the biocompatible polar aprotic organic liquid to dissipate to produce a solid or gel biodegradable implant. Preferably, the biodegradable solid or gel implant releases an effective amount of rapamycin or rapamycin derivative by diffusion, erosion, or a combination of diffusion and erosion as the solid or gel implant biodegrades in the patient.

The present invention also is directed to a method of treating or preventing mammalian diseases that are ameliorated, cured or prevented by rapamycin and its derivatives. The method includes administering, to a patient (preferably a human patient) in need of such treatment or prevention, an effective amount of a flowable composition as described herein. Specifically, the diseases can be those that have an etiology associated with proliferative problems or inflammation, including those concerning proliferative disorders or inflammation of the eye. Especially, these diseases include those concerning ocular conditions such as ocular neovascularization, for example choroidal neovascularization, or inflammation, and more preferably the malcondition is an inflammatory disease such as uveitis, or a diabetic eye disease such as diabetic retinopathy or diabetic macular edema, as well as fibrovascular conditions of the eye.

The present invention also is directed to a kit. Such a kit is suitable for in situ formation of a biodegradable implant in a body. The kit can include a container that includes a flowable composition. The composition can include a biodegradable thermoplastic polymer that is at least substantially insoluble in body fluid, a biocompatible polar aprotic organic liquid, and rapamycin or a rapamycin derivative. The kit can alternatively include a first container and a second container. The first container includes a composition of the biodegradable thermoplastic polymer and the biocompatible polar aprotic organic liquid. The second container includes rapamycin or a rapamycin derivative. These ingredients, their properties, and preferred amounts are as disclosed above. Preferably, the first container is a syringe and the second container is a syringe. In addition, the rapamycin is preferably lyophilized. The kit can preferably include instructions. Preferably, the first container can be connected to the second container. More preferably, the first container and the second container are each configured to be directly connected to each other. More preferably, the first container and the second container are each configured to be directly connected to each other. In another preferred embodiment, the composition of the biodegradable thermoplastic polymer, the biocompatible polar aprotic organic liquid and the rapamycin, are contained in a single container. Preferably, the container is a syringe.

The present invention also is directed to a solid or gel implant. The solid or gel implant is composed of at least the biocompatible thermoplastic polymer and rapamycin or a rapamycin derivative and is substantially insoluble in body fluid. While rapamycin itself has at least some solubility in body fluid, its isolation within the substantially insoluble implant allows for its slow, sustained release into the body.

The solid implant has a solid matrix or a solid microporous matrix while the gel implant has a gelatinous matrix. The matrix can be a core surrounded by a skin. When microporous, the core preferably contains pores of diameters from about 1 to about 1000 microns. When microporous, the skin preferably contains pores of smaller diameters than those of the core pores. In addition, the skin pores are preferably of a size such that the skin is functionally non-porous in comparison with the core.

The solid or gel implant can optionally include one or more biocompatible organic substances which may function as an excipient as described above, or which may function as a plasticizer, a sustained release profile modifier, emulsifier and/or isolation carrier for rapamycin.

The biocompatible organic liquid may also serve as an organic substance of the implant and/or may provide an additional function such as a plasticizer, a modifier, an emulsifier or an isolation carrier. There may be two or more organic liquids present in the flowable composition such that the primary organic liquid acts as a mixing, solubilizing or dispersing agent, and the supplemental organic liquid or liquids provide additional functions within the flowable composition and the implant. Alternatively, there may be one organic liquid which at least may act as a mixing, solubilizing or dispersing agent for the other components, and may provide additional functions as well. As second or additional components, additional kinds of biodegradable organic liquids typically are combined with the flowable composition and may remain with the implant as the administered flowable composition coagulates.

When serving as a plasticizer, the biocompatible organic substance provides such properties as flexibility, softness, moldability and drug release variation to the implant. When serving as a modifier, the biocompatible organic substance also provides the property of rapamycin release variation to the implant. Typically, the plasticizer increases the rate of rapamycin release while the modifier slows the rate of rapamycin release. Also, there can be structural overlap between these two kinds of organic substances functioning as plasticizers and rate modifiers.

When serving as an emulsifier, the biocompatible organic substance at least in part enables a uniform mixture of the rapamycin within the implant.

When serving as an isolation carrier, the biocompatible organic substance will function to encapsulate, isolate or otherwise surround molecules or nanoparticles of the rapamycin or rapamycin derivative so as to prevent its burst at least in part, and to isolate the rapamycin from degradation by other components of the flowable composition and implant.

The amount of biocompatible organic substance optionally remaining in the solid or gel implant is preferably minor, such as from about 0 wt. % (or an almost negligible amount) to about 20 wt. % of the composition. In addition, the amount of biocompatible organic substance optionally present in the solid or gel implant preferably decreases over time.

DEFINITIONS

Figure 1:
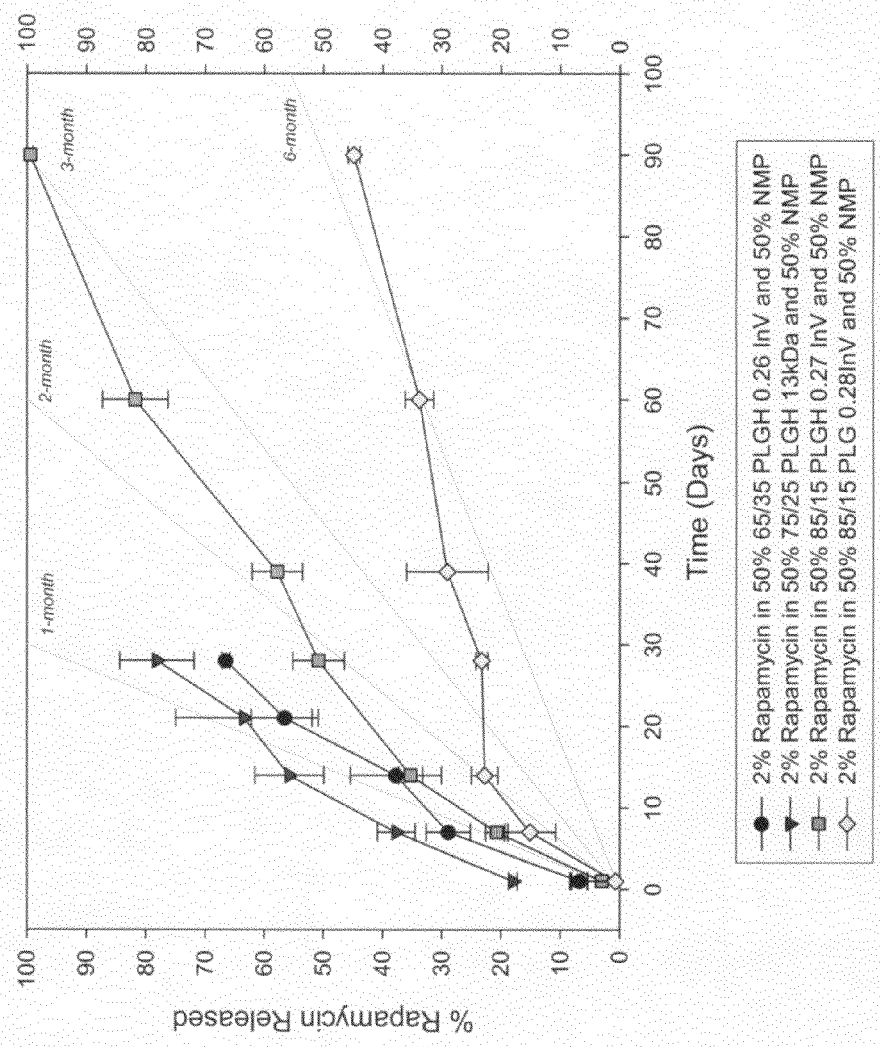
FIG. 1 is a graphical representation of the subcutaneous rapamycin release from various Rapamycin/ATRIGEL® formulations over a 90-day time period.

The words and phrases presented in this patent application have their ordinary meanings to one of skill in the art unless otherwise indicated. Such ordinary meanings can be obtained by reference to their use in the art and by reference to general and scientific dictionaries such as Webster's New World Dictionary, Simon & Schuster, publishers, New York, N.Y., 1995; The American Heritage Dictionary of the English Language, Houghton Mifflin, Boston Mass., 1981; Hawley's Condensed Chemical Dictionary $14^{th}$ edition, I. Sax, editor, Wiley Europe, 2002.

The following explanations of certain terms are meant to be illustrative rather than exhaustive. These terms have their ordinary meanings given by usage in the art and in addition include the following explanations.

The term "and/or" means any one of the items, any combination of the items, or all of the items with which this term is associated.

As used herein, the singular forms "a," "an," and "the" include plural reference unless the context clearly dictates otherwise. Thus, for example, a reference to "a formulation" includes a plurality of such formulations, so that a formulation of compound X includes formulations of compound X.

The term "biocompatible" means that the material, substance, compound, molecule, polymer or system to which it applies will not cause severe toxicity, severe adverse biological reaction, or lethality in an animal to which it is administered at reasonable doses and rates.

The term "biodegradable" means that the material, substance, compound, molecule, polymer or system is cleaved, oxidized, hydrolyzed or otherwise broken down by hydrolytic, enzymatic or another mammalian biological process for metabolism to chemical units that can be assimilated or eliminated by the mammalian body.

The term "bioerodable" means that the material, substance, compound, molecule, polymer or system is biodegraded or mechanically removed by a mammalian biological process so that new surface is exposed.

As used herein, the term "cell proliferation" means any increase in the number of cells as a result of cell growth and cell division. This includes cells that are grown in culture and cells that are present in a living organism. Cell proliferation includes the new growth of cells in a region or section of an organism or cell culture where those cells had not existed before. Cell proliferation also includes the continued or new growth of cells that are already present in any given region or section of an organism or cell culture.

As used herein, the term "flowable" refers to the ability of the "flowable" composition to be transported under pressure into the body of a patient. For example, the flowable composition can have a low viscosity like water, and be injected with the use of a syringe, beneath the skin of a patient. The flowable composition can alternatively have a high viscosity as in a gel and can be placed into a patient through a high pressure transport device such as a high pressure syringe, cannula, needle and the like. The ability of the composition to be injected into a patient will typically depend upon the viscosity of the composition. The composition will therefore have a suitable viscosity ranging from low like water to high like a gel, such that the composition can be forced through the transport device (e.g., syringe) into the body of a patient.

As used herein, a "gel" is a substance having a gelatinous, jelly-like, or colloidal properties. *Concise Chemical and Technical Dictionary*, 4th Enlarged Ed., Chemical Publishing Co., Inc., p. 567, NY, N.Y. (1986).

The term "heterocyclic" refers to any cyclic organic compound containing one or more nitrogen and/or oxygen and/or sulfur atoms in its cyclic structure. A heterocyclic compound may be saturated or unsaturated but is not aromatic.

As used herein, "inflammation" refers to a process that occurs in affected cells and adjacent tissues in response to an injury or abnormal stimulation caused by a physical, chemical, or biologic substance. Inflammation is characterized by redness, heat, swelling, pain and dysfunction of the organs involved. The cellular component of inflammation involves the movement and proliferation of multiple cell types including mast cells, basophils, eosinophils, neutrophils, macrophages, monocytes, T cells, B cells, and natural killer cells. Disorders associated with inflammation include rheumatoid arthritis, shoulder tendonitis or bursitis, gouty arthritis, polymyalgia rheumatica, appendicitis, arteritis, blepharitis, bronchiolitis, bronchitis, bursitis, cervicitis, cholangitis, cholecystitis, chorioamnionitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, gingivitis, hepatitis, hidradenitis suppurativa, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis and pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

As used herein, a "liquid" is a substance that undergoes continuous deformation under a shearing stress. *Concise Chemical and Technical Dictionary*, 4th Enlarged Ed., Chemical Publishing Co., Inc., p. 707, NY, N.Y. (1986).

The term "rapamycin" is described in the following rapamycin section. "Rapamycin" includes rapamycin and rapamycin derivatives.

The term "polymer" means a molecule of one or more repeating monomeric residue units covalently bonded together by one or more repeating chemical functional groups. The term includes all polymeric forms such as linear, branched, star, random, block, graft and the like. It includes homopolymers formed from a single monomer, copolymer formed from two or more monomers, terpolymers formed from three or more polymers and polymers formed from more than three monomers. Differing forms of a polymer may also have more than one repeating, covalently bonded functional group.

The term polyester refers to polymers containing monomeric repeats, at least in part, of the linking group: —OC(=O)— or —C(=O)O—.

The term polyanhydride refers to polymers containing monomeric repeats, at least in part, of the linking group —C(=O)—O—C(=O)—.

The term polycarbonate refers to polymers containing monomeric repeats, at least in part, of the linking group —OC(=O)O—.

The term polyurethane refers to polymers containing monomeric repeats, at least in part, of the linking group —NHC(=O)O—.

The term polyurea refers to polymers containing monomeric repeats, at least in part, of the linking group —NHC(=O)NH—.

The term polyamide refers to polymers containing monomeric repeats, at least in part, of the linking group —C(=O)NH—.

The term polyether refers to polymers containing monomeric repeats, at least in part, of the linking group —O—.

The term polyacetal refers to polymers containing monomeric repeats, at least in part, of the linking group —CHR—O—CHR—.

The term polyketal refers to polymers containing monomeric repeats, at least in part, of the linking group —CR$_2$—O—CR$_2$—.

The term "skin" and the term "core" of a skin and core matrix mean that a cross section of the matrix will present a discernable delineation between an outer surface and the inner portion of the matrix. The outer surface is the skin and the inner portion is the core.

The term "thermoplastic" as applied to a polymer means that the polymer repeatedly will melt upon heating and will solidify upon cooling. It signifies that no or only a slight degree of cross-linking between polymer molecules is present. It is to be contrasted with the term "thermoset" which indicates that the polymer will set or substantially cross-link upon heating or upon application of a similar reactive process and will then no longer undergo melt-solidification cycles upon heating and cooling.

As used herein, "ocular" or "ocular region" refers to the eye, surrounding tissues, and to bodily fluids in the region of the eye. Specifically, the term includes the cornea or the sclera or the uvea, the conjunctiva (e.g., bulbar conjunctiva, palpebral conjunctiva, and tarsal conjunctiva), anterior chamber, lacrimal sac, lacrimal canals, lacrimal ducts, medial canthus, nasolacrimal duct, and the eyelids (e.g., upper eyelid and lower eyelid). Additionally, the term includes the inner surface of the eye (conjunctiva overlying the sclera), and the inner surface of the eyelids (palpepral conjunctiva).

As used herein, "conjunctiva" refers to the mucous membrane lining the inner surfaces of the eyelids and anterior part of the sclera. The "palpebral conjunctiva" lines the inner surface of the eyelids and is thick, opaque, and highly vascular. The "bulbar conjunctiva" is loosely connected, thin, and transparent, covering the sclera or the anterior third of the eye.

As used herein, "cornea" refers to the convex, transparent anterior part of the eye, comprising one sixth of the outermost tunic of the eye bulb. It allows light to pass through it to the lens. The cornea is a fibrous structure with five layers: the anterior corneal epithelium, continuous with that of the conjunctiva; the anterior limiting layer (Bowman's membrane); the substantial propria; the posterior limiting layer (Descemet's membrane); and the endothelium of the anterior chamber (keratoderma). It is dense, uniform in thickness, and nonvascular, and it projects like a dome beyond the sclera, which forms the other five sixths of the eye's outermost tunic. The degree of corneal curvature varies among different individuals and in the same person at different ages; the curvature is more pronounced in youth than in advanced age.

As used herein, "eye" refers to one of a pair of organs of sight, contained in a bony orbit at the front of the skull, embedded in orbital fat, and innervated by four cranial nerves: optic, oculomotor, trochlear, and abducens. Associated with the eye are certain accessory structures, such as the muscles, the fasciae, the eyebrow, the eyelids, the conjunctiva, and the lacrimal gland. The bulb of the eye is composed of segments of two spheres with nearly parallel axes that constitute the outside tunic and one of three fibrous layers enclosing two internal cavities separated by the crystalline lens. The smaller cavity anterior to the lens is divided by the iris into two chambers, both filled with aqueous humor. The posterior cavity is larger than the anterior cavity and contains the jellylike vitreous body that is divided by the hyaloid canal. The outside tunic of the bulb consists of the transparent cornea anteriorly, constituting one fifth of the tunic, and the opaque sclera posteriorly, constituting five sixths of the tunic. The intermediate vascular, pigmented tunic consists of the choroid, the ciliary body, and the iris. The internal tunic of nervous tissue is the retina. Light waves passing through the lens strike a layer of rods and cones in the retina, creating impulses that are transmitted by the optic nerve to the brain. The transverse and the anteroposterior diameters of the eye bulb are slightly greater than the vertical diameter; the bulb in women is usually smaller than the bulb in men. Eye movement is controlled by six muscles: the superior and inferior oblique muscles and the superior, inferior, medial, and lateral rectus muscles. Also called bulbus oculi, eyeball.

As used herein, "eyelid" refers to a movable fold of thin skin over the eye, with eyelashes and ciliary and meibomian glands along its margin. It consists of loose connective tissue containing a thin plate of fibrous tissue lined with mucous membrane (conjunctiva). The orbicularis oculi muscle and the oculomotor nerve control the opening and closing of the eyelid. The upper and lower eyelids are separated by the palpebral fissure. Also called palpebra.

As used herein, "retina" refers to a 10-layered, delicate nervous tissue membrane of the eye, continuous with the optic nerve, that receives images of external objects and transmits visual impulses through the optic nerve to the brain. The retina is soft and semitransparent and contains rhodopsin. It consists of the outer pigmented layer and the nine-layered retina proper. These nine layers, starting with the most internal, are the internal limiting membrane, the stratum opticum, the ganglion cell layer, the inner plexiform layer, the inner nuclear layer, the outer plexiform layer, the outer nuclear layer, the external limiting membrane, and the layer of rods and cones. The outer surface of the retina is in contact with the choroid; the inner surface with the vitreous body. The retina is thinner anteriorly, where it extends nearly as far as the ciliary body, and thicker posteriorly, except for a thin spot in the exact center of the posterior surface where focus is best. The photoreceptors end anteriorly in the jagged ora serrata at the ciliary body, but the membrane of the retina extends over the back of the ciliary processes and the iris. The retina becomes clouded and opaque if exposed to direct sunlight. See also Jacob's membrane, macula, optic disc.

As used herein, "sclera" refers to the tough inelastic opaque membrane covering the posterior five sixths of the eyebulb. It maintains the size and form of the bulb and attaches to muscles that move the bulb. Posteriorly it is pierced by the optic nerve and, with the transparent cornea, makes up the outermost of three tunics covering the eyebulb.

As used herein, "uvea" refers to the fibrous tunic beneath the sclera that includes the iris, the ciliary body, and the choroid of the eye.

As used herein, "vasculature" refers to the distribution of blood vessels in an organ or tissue.

As used herein, "treating" or "treat" or "treatment" includes (i) preventing a pathologic condition (e.g., a solid tumor) from occurring (e.g. prophylaxis); (ii) inhibiting the pathologic condition (e.g., a solid tumor) or arresting its development; and (iii) relieving the pathologic condition (e.g., relieving the symptoms associated with a solid tumor).

As used herein, "effective amount" is intended to include an amount of rapamycin or a derivative thereof or any combination of those useful in the present invention to treat or prevent the underlying disorder or disease, or to treat the symptoms associated with the underlying disorder or disease in a host. Synergy, as described for example by Chou and Talalay, Adv. Enzyme Regul. 22:27-55 (1984), occurs when the effect of rapamycin or a derivative thereof when administered in combination is greater than the additive effect of the rapamycin or a derivative thereof when administered alone as a single agent. In general, a synergistic effect is most clearly demonstrated at suboptimal concentrations of the rapamycin or derivative thereof. Synergy can be in terms of lower cytotoxicity, increased activity, or some other beneficial effect of the combination compared with the individual components.

DESCRIPTION OF THE INVENTION

The present invention is directed to a rapamycin sustained release delivery system. The sustained release delivery system includes a flowable composition as described herein that is capable of providing a gel or solid implant of the invention. The delivery system provides an in situ sustained release of rapamycin or a rapamycin derivative. The flowable composition accomplishes the sustained release through its use to produce the implant of the invention. The implant has a low implant volume and provides a long term delivery of rapamycin. The flowable composition enables subcutaneous formation of the implant in situ and causes little or no tissue necrosis.

The flowable composition as described herein is a combination of a biodegradable, at least substantially water-insoluble thermoplastic polymer, a biocompatible polar aprotic organic liquid and rapamycin or a rapamycin derivative. The polar, aprotic organic liquid has a solubility in body fluid ranging from practically insoluble to completely soluble in all proportions. Preferably, the thermoplastic polymer is a thermoplastic polyester of one or more hydroxycarboxylic acids or one or more diols and dicarboxylic acids. Especially preferably, the thermoplastic polymer is a polyester of one or more hydroxylcarboxyl dimers such as lactide, glycolide, dicaprolactone and the like.

Specific and preferred biodegradable thermoplastic polymers and polar aprotic solvents; concentrations of thermoplastic polymers, polar aprotic organic liquids, rapamycin, and molecular weights of the thermoplastic polymer; and weight or mole ranges of components of the solid implant described herein are exemplary. They do not exclude other biodegradable thermoplastic polymers and polar aprotic organic liquids; other concentrations of thermoplastic polymers, polar aprotic liquids, rapamycin, or molecular weights of the thermoplastic polymer; derivatives of rapamycin; and components within the solid implant.

The present invention is directed to a flowable composition suitable for use in providing a controlled sustained release implant, a method for forming the flowable composition, a method for using the flowable composition, the biodegradable sustained release solid or gel implant that is formed from the flowable composition, a method of forming the biodegradable implant in situ, a method for treating disease through use of the biodegradable implant and a kit that includes the flowable composition. The flowable composition may preferably be used to provide a biodegradable or bioerodible microporous in situ formed implant in animals.

The flowable composition is composed of a biodegradable thermoplastic polymer in combination with a biocompatible polar aprotic organic liquid and rapamycin. The biodegradable thermoplastic polymer is substantially insoluble in aqueous medium and/or in body fluid, biocompatible, and biodegradable and/or bioerodible within the body of a patient. The flowable composition may be administered as a liquid or gel to tissue and forms an implant in situ.

Alternatively, the implant may be formed ex vivo by combining the flowable composition with an aqueous medium. In this embodiment, the preformed implant may be surgically administered to the patient.

In either embodiment, the thermoplastic polymer coagulates or solidifies to form the solid or gel implant upon the dissipation, dispersement or leaching of the organic liquid from the flowable composition when the flowable composition contacts a body fluid, an aqueous medium or water. The coagulation or solidification entangles and entraps the other components of the flowable composition such as rapamycin or a rapamycin derivative, excipients, organic substances and the like so that they become dispersed within the gelled or solidified implant matrix. The release rate of drugs from this type of delivery system can be controlled by the type and molecular weight of the polymer and drug load of the constituted product. Therefore, the system can be tailored to meet the specific needs of the patient.

The flowable composition is biocompatible and the polymer matrix of the implant does not cause substantial tissue irritation or necrosis at the implant site. Furthermore, the implant does not float in the vitreous when injected intravitreally, due to the anchoring of the implant to the inner surface of the eye. Similarly, the subconjuctivally and sub-tenons injected implants adhere to the outer surface of the eye due to the tackiness of the implant. The implant delivers a sustained level of rapamycin to the patient. Preferably, the flowable composition can be a liquid or a gel, suitable for injection in a patient (e.g., human).

The present invention improves the bioavailability of a sustained release formulation of rapamycin. The sustained release of rapamycin from an implant of the invention has the ability to inhibit abnormal cellular proliferation, which includes neovascularization, fibrosis, lymphoid proliferation, inflammation, and/or neoplastic growth occurring in any tissue, but particularly in ocular tissues. In the case of ocular tissues, unexpected efficacy provided by the composition and implant of the invention enables relatively high bioavailability of rapamycin, because: (1) the blood-retinal barrier limits penetration into the ocular tissues; and (2) the flowable composition and implant as described herein demonstrate surprising anti-inflammatory and non-inflammatory properties.

In addition, the flowable composition and methods herein provide: (a) relatively low volume injections; (b) improved local tissue tolerance at the injection site; (c) an opportunity to use a subcutaneous, or an intraocular, injection rather than an intramuscular injection; (d) infrequent injections; and (e) the unexpected result of no blockage of receipt of light by the retina.

According to the present invention, the rapamycin sustained release delivery system provides several advantages that increase the efficacy, safety, and convenience of rapamycin used to treat any rapamycin-responsive disease or medical condition. This includes non-ocular and ocular diseases. The invention is particularly useful for the treatment of ocular diseases, and most particularly, for the treatment of proliferative and inflammatory diseases of the eye. Examples of such diseases include, but are not limited to, uveitis, neoplasia, retinal or choroidal neovascularizaton occurring in diabetic retinopathy and age-related macular degeneration, and diabetic macular edema.

By comparison to formulations derived from other sustained release drug delivery technologies, the rapamycin sustained release delivery system is designed to provide: (a) favorable release kinetics with minimal burst; (b) increased duration of drug release with less frequent injections; (c) improved bioavailability; (d) improved local tissue tolerance due to a small injection volume; (e) limited irritation and inflammation upon and after administration; (f) the ability to use subcutaneous or intraocular injection rather than intramuscular injection; and (g) the absence of impairment of vision due to the placement and "plug" aspect of the system. Taken together, these features make a highly beneficial rapamycin sustained release delivery system.

Biodegradable Thermoplastic Polymer

Biodegradable polymers have been employed in many medical applications, including drug delivery devices. The drug is generally incorporated into the polymeric composition and formed into the desired shape outside the body. This solid implant is then typically inserted into the body of a human, animal, bird, and the like through an incision. Alternatively, small discrete particles composed of these polymers can be injected into the body by a syringe. Preferably, however, certain of these polymers can be injected via syringe as a liquid polymeric composition.

Liquid polymeric compositions useful for biodegradable controlled release drug delivery systems are described, e.g., in U.S. Pat. Nos. 4,938,763; 5,702,716; 5,744,153; 5,990,194; and 5,324,519. These compositions are administered to the body in a liquid state or, alternatively, as a solution, typically via syringe. Once in the body, the composition coagulates into a solid. One type of polymeric composition includes a nonreactive thermoplastic polymer or copolymer dissolved in a body fluid-dispersible solvent. This polymeric solution is placed into the body where the polymer congeals or precipitatively solidifies upon the dissipation or diffusion of the solvent into the surrounding body tissues.

The flowable composition described herein is produced by combining a solid, biodegradable thermoplastic polymer and rapamycin and a biocompatible polar aprotic organic liquid. The flowable composition can be administered by a syringe and needle to a patient in need of treatment. Any suitable biodegradable thermoplastic polymer can be employed, provided that the biodegradable thermoplastic polymer is at least substantially insoluble in body fluid.

The biocompatible, biodegradable, thermoplastic polymer used according to the invention can be made from a variety of monomers which form polymer chains or monomeric units joined together by linking groups. The thermoplastic polymer is composed of a polymer chain or backbone containing monomeric units joined by such linking groups as ester, amide, urethane, anhydride, carbonate, urea, esteramide, acetal, ketal, and orthocarbonate groups as well as any other organic functional group that can be hydrolyzed by enzymatic or hydrolytic reaction (i.e., is biodegradable by this hydrolytic action). The thermoplastic polymer is usually formed by reaction of starting monomers containing the reactant groups that will form the backbone linking groups. For example, alcohols and carboxylic acids will form ester linking groups. Isocyanates and amines or alcohols will respectively form urea or urethane linking groups.

Any aliphatic, aromatic or arylalkyl starting monomer having the specified functional groups can be used according to the invention to make the thermoplastic polymers of the invention, provided that the polymers and their degradation products are biocompatible. The monomer or monomers used in forming the thermoplastic polymer may be of a single or multiple identity. The resultant thermoplastic polymer will be a homopolymer formed from one monomer, or one set of monomers such as when a diol and diacid are used, or a copolymer, terpolymer, or multi-polymer formed from two or more, or three or more, or more than three monomers or sets of monomers. The biocompatibility specifications of such starting monomers are known in the art.

The thermoplastic polymers useful according to the invention are substantially insoluble in aqueous media and body fluids, preferably essentially completely insoluble in such media and fluids. They are also capable of dissolving or dispersing in selected organic liquids having a water solubility ranging from completely soluble in all proportions to water insoluble. The thermoplastic polymers also are biocompatible.

When used in the flowable composition described herein, the thermoplastic polymer in combination with the organic liquid provides a viscosity of the flowable composition that varies from low viscosity, similar to that of water, to a high viscosity, similar to that of a paste, depending on the molecular weight and concentration of the thermoplastic polymer. Typically, the polymeric composition includes about 10 wt. % to about 95 wt. %, more preferably about 20 wt. % to about 70 wt. %, most preferably about 30 wt. % to about 65 wt. %, of a thermoplastic polymer.

According to the present invention, the biodegradable, biocompatible thermoplastic polymer can be a linear polymer, it can be a branched polymer, or it can be a combination thereof. Any option is available according to the present invention. To provide a branched thermoplastic polymer, some fraction of one of the starting monomers may be at least trifunctional, and preferably multifunctional. This multifunctional character provides at least some branching of the resulting polymer chain. For example, when the polymer chosen contains ester linking groups along its polymer backbone, the starting monomers normally will be hydroxycarboxylic acids, cyclic dimers of hydroxycarboxylic acids, cyclic trimers of hydroxycarboxylic acids, diols or dicarboxylic acids. Thus, to provide a branched thermoplastic polymer, some fraction of a starting monomer that is at least multifunctional, such as a triol or a tricarboxylic acid is included within the combination of monomers being polymerized to form the thermoplastic polymer used according to the invention. In addition, the polymers of the present invention may incorporate more than one multifunctional unit per polymer molecule, and typically many multifunctional units depending on the stoichiometry of the polymerization reaction. The polymers of the present invention may also optionally incorporate at least one multifunctional unit per polymer molecule. A so-called star or branched polymer is formed when one multifunctional unit is incorporated in a polymer molecule.

According to the invention, the preferred thermoplastic polyester may be formed from such monomers as hydroxycarboxylic acids or dimers therefor. Alternatively, a thermoplastic polyester may be formed from a dicarboxylic acid and a diol. A branching monomer such as a dihydroxycarboxylic acid would be included with the first kind of starting monomer, or a triol and/or a tricarboxylic acid would be included with the second kind of starting monomer if a branched polyester were desired. Similarly, a triol, tetraol, pentaol, or hexaol such as sorbitol or glucose can be included with the first kind of starting monomer if a branched or star polyester were desired. The same rationale would apply to polyamides. A triamine and/or triacid would be included with starting monomers of a diamine and dicarboxylic acid. An amino dicarboxylic acid, diamino carboxylic acid or a triamine would be included with the second kind of starting monomer, amino acid. Any aliphatic, aromatic or arylalkyl starting monomer having the specified functional groups can be used to make the branched thermoplastic polymers of the invention, provided that the polymers and their degradation products are biocompatible. The biocompatibility specifications of such starting monomers are known in the art.

The monomers used to make the biocompatible thermoplastic polymers of the present invention will produce polymers or copolymers that are thermoplastic, biocompatible and biodegradable. Examples of thermoplastic, biocompatible, biodegradable polymers suitable for use as the biocompatible thermoplastic branched polymers of the present invention include polyesters, polylactides, polyglycolides, polycaprolactones, polyanhydrides, polyamides, polyurethanes, polyesteramides, polydioxanones, polyacetals, polyketals, polycarbonates, polyorthocarbonates, polyorthoesters, polyphosphoesters, polyphosphazenes, polyhydroxybutyrates, polyhydroxyvalerates, polyalkylene oxalates, polyalkylene succinates, poly(malic acid), poly(amino acids), and copolymers, terpolymers, or combinations or mixtures of the above materials. Suitable examples of such biocompatible, biodegradable, thermoplastic polymers are disclosed, e.g., in U.S. Pat. Nos. 4,938,763; 5,278,201; 5,324,519; 5,702,716; 5,744,153; 5,990,194; 6,461,631 and 6,565,874.

The polymer composition of the invention can also include polymer blends of the polymers of the present invention with other biocompatible polymers, so long as they do not interfere undesirably with the biodegradable characteristics of the composition. Blends of the polymer of the invention with such other polymers may offer even greater flexibility in designing the precise release profile desired for targeted drug delivery or the precise rate of biodegradability desired for implants such as ocular implants.

The preferred biocompatible thermoplastic polymers or copolymers of the present invention are those which have a lower degree of crystallization and are more hydrophobic.

These polymers and copolymers are more soluble in the biocompatible organic liquids than highly crystalline polymers such as polyglycolide, which has a high degree of hydrogen-bonding. Preferred materials with the desired solubility parameters are polylactides, polycaprolactones, and copolymers of these with glycolide so as to provide more amorphous regions to enhance solubility. Generally, the biocompatible, biodegradable thermoplastic polymer is substantially soluble in the organic liquid so that solutions, dispersions or mixtures up to 50-60 wt % solids can be made. Preferably, the polymers used according to the invention are essentially completely soluble in the organic liquid so that solutions, dispersions or mixtures up to 85-98 wt % solids can be made. The polymers also are at least substantially insoluble in water so that less than 0.1 g of polymer per mL of water will dissolve or disperse in water. Preferably, the polymers used according to the invention are essentially completely insoluble in water so that less than 0.001 g of polymer per mL of water will dissolve or disperse in water. At this preferred level, the flowable composition with a completely water miscible organic liquid will almost immediately transform to the solid implant.

Optionally, the delivery system may also contain a combination of a non-polymeric material and an amount of a thermoplastic polymer. The combination of non-polymeric material and thermoplastic polymer may be adjusted and designed to provide a more coherent rapamycin sustained release delivery system.

Non-polymeric materials useful in the present invention are those that are biocompatible, substantially insoluble in water and body fluids, and biodegradable and/or bioerodible within the body of an animal. The non-polymeric material is capable of being at least partially solubilized in an organic liquid. In the flowable composition described herein containing some organic liquid or other additive, the non-polymeric materials are also capable of coagulating or solidifying to form a solid or gel implant upon the dissipation, dispersement or leaching of the organic liquid component from the flowable composition upon contact of the flowable composition with a body fluid. The matrix of all embodiments of the implant including a non-polymeric material will have a consistency ranging from gelatinous to impressionable and moldable, to a hard, dense solid.

Non-polymeric materials that can be used in the delivery system generally include any having the foregoing characteristics. Examples of useful non-polymeric materials include sterols such as cholesterol, stigmasterol, beta-sistosterol, and estradiol; cholesteryl esters such as cholesteryl stearate, C18-C36 mono-, di-, and tricylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl tridocosanoate, glyceryl trimyristate, glyceryl tridecenoate, glyceryl tristearate and mixtures thereof; sucrose fatty acid esters such as sucrose distearate and sucrose palmitate; sorbitan fatty acid esters such as sorbitan monostearate, sorbitan monopalmitate, and sorbitan tristearate; C16-C18 fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Preferred non-polymeric materials include cholesterol, glyceryl monostearate, glyceryl tristearate, stearic acid, stearic anhydride, glyceryl monooleate, glyeryl monolinoleate, and acetylated monoglyerides.

The polymeric and non-polymeric materials may be selected and/or combined to control the rate of biodegradation, bioerosion and/or bioabsorption within the implant site. Generally, the implant matrix will breakdown over a period from about 1 week to about 12 months, preferably over a period of about 1 week to about 6 months.

Thermoplastic Polymer Molecular Weight

The molecular weight of the polymer used in the present invention can affect the rate of rapamycin or rapamycin derivative release from the implant. Under these conditions, as the molecular weight of the polymer increases, the rate of rapamycin release from the system decreases. This phenomenon can be advantageously used in the formulation of systems for the controlled release of rapamycin or a rapamycin derivative. For relatively quick release of rapamycin, low molecular weight polymers can be chosen to provide the desired release rate. For release of rapamycin over a relatively long period of time, a higher polymer molecular weight can be chosen. Accordingly, a rapamycin sustained release delivery system can be produced with an optimum polymer molecular weight range for the release of rapamycin over a selected length of time.

The molecular weight of a polymer can be varied by any of a variety of methods. The choice of method is typically determined by the type of polymer composition. For example, if a thermoplastic polyester is used that is biodegradable by hydrolysis, the molecular weight can be varied by controlled hydrolysis, such as in a steam autoclave. Typically, the degree of polymerization can be controlled, for example, by varying the number and type of reactive groups and the reaction times.

The control of molecular weight and/or inherent viscosity of the thermoplastic polymer is a factor involved in the formation and performance of the implant. In general, thermoplastic polymers with higher molecular weight and higher inherent viscosity will provide an implant with a slower degradation rate and therefore a longer duration. Changes and fluctuations of the molecular weight of the thermoplastic polymer following the compounding of the delivery system will result in the formation of an implant that shows a degradation rate and duration substantially different from the degradation rate and duration desired or predicted.

The thermoplastic polymers useful according to the invention may have average molecular weights ranging from about 1 kiloDalton (kD) to about 1,000 kD, preferably from about 2 kD to about 500 kD, more preferably from abut 5 kD to about 200 kD, and more preferably from about 5 kD to about 100 kD, and even more preferably from about 10 kD to about 75 kD. The molecular weight may also be indicated by the inherent viscosity (abbreviated as "I.V.", units are in deciliters/gram). Generally, the inherent viscosity of the thermoplastic polymer is a measure of its molecular weight and degradation time (e.g., a thermoplastic polymer with a high inherent viscosity has a higher molecular weight and longer degradation time). Preferably, the thermoplastic polymer has a molecular weight, as shown by the inherent viscosity, from about 0.05 dL/g to about 2.0 dL/g (as measured in chloroform), more preferably from about 0.10 dL/g to about 1.5 dL/g.

Characteristics of Preferred Polyester

The preferred thermoplastic biodegradable polymer of the flowable composition is a polyester. Generally, the polyester may be composed of units of one or more hydroxycarboxylic acid residues wherein the distribution of differing units may be random, block, paired or sequential. Alternatively, the polyester may be composed of units of one or more diols and one or more dicarboxylic acids. The distribution will depend upon the starting materials used to synthesize the polyester and upon the process for synthesis. An example of a polyester composed of differing paired units distributed in block or sequential fashion is a poly(lactide-co-glycolide). An example of a polyester composed of differing unpaired units distributed in random fashion is poly(lactic acid-co-glycolic acid). Other examples of suitable biodegradable thermoplastic polyesters include polylactides, polyglycolides, polycaprolactones, copolymers thereof, terpolymers thereof, and any combinations thereof. Preferably, the suitable biodegradable thermoplastic polyester is a polylactide, a polyglycolide, a copolymer thereof, a terpolymer thereof, or a combination thereof.

The terminal groups of the polyester can either be hydroxyl, carboxyl, or ester depending upon the method of polymerization. For example, polycondensation of lactic or glycolic acid will provide a polymer with terminal hydroxyl and carboxyl groups. Ring-opening polymerization of the cyclic lactide or glycolide monomers with water, lactic acid, or glycolic acid will provide polymers with these same terminal groups. However, ring-opening of the cyclic monomers with a monofunctional alcohol such as methanol, ethanol, or 1-dodecanol will provide a polymer with one hydroxyl group and one ester terminal group. Ring-opening polymerization of the cyclic monomers with a polyol such as glucose, 1,6-hexanediol or polyethylene glycol will provide a polymer with only hydroxyl terminal groups. Such a polymerization of dimers of hydroxylcarboxylic acids and a polyol is a chain extension of the polymer. The polyol acts as a central condensation point with the polymer chain growing from the hydroxyl groups incorporated as ester moieties of the polymer. The polyol may be a diol, triol, tetraol, pentaol or hexaol of 2 to 30 carbons in length. Examples include saccharides, reduced saccharides such as sorbitol, diols such as hexane-1, 6-diol, triols such as glycerol or reduced fatty acids, and similar polyols. Generally, the polyesters copolymerized with alcohols or polyols will provide longer duration implants.

A sample of a preferred biodegradable thermoplastic polyester polymer of the invention has a distribution of molecular weights among the individual molecules making up the sample. The molecular weight distribution of a polymer sample as obtained directly from a polymerization reaction can be further modified according to the present invention through selective enrichment of higher molecular weight fractions of the polymer using selective precipitation. For example, the molecular weight distribution of a sample of a polymer of the invention can be modified by selective precipitation so as to remove lower molecular weight components and leave behind higher molecular weight components, as is known to reduce the initial burst effect when the polymer is a component of a controlled sustained release implant. A polymer sample that is obtained such as by polymerization of dimers as described above is dissolved in a liquid that is a solvent for the entire sample, for example methylene chloride, then this solution is mixed with a liquid that is a non-solvent for the polymer, for example methanol or a hydrocarbon. As the proportion of non-solvent in the liquid mixture increases during the mixing process, precipitation of the polymer takes place such that higher molecular weight components aggregate as solids while leaving at least a portion of the lower molecular weight components, for example those molecules having molecular weights of a few thousand daltons, dissolved in the supernatant liquid. The solid polymeric material, that can be separated from the liquid by filtration, centrifugation, or the like, has a distribution of molecular weights that is skewed towards higher molecular weights relative to a sample of the polymer prior to the step of selective precipitation.

The present invention provides a biocompatible, biodegradable PLG low-burst copolymer material adapted for use in a controlled release formulation, the low-burst copolymer material being characterized by a weight average molecular weight of about 10 kilodaltons to about 50 kilodaltons and a polydispersity index of about 1.4-2.0, and being further characterized by having separated therefrom a copolymer fraction characterized by a weight average molecular weight of about 4 kDa to about 10 kDa and a polydispersity index of about 1.4 to 2.5 (hereinafter the "removed copolymer fraction"). The inventive PLG low-burst copolymer material is prepared from a starting PLG copolymer material without a step of hydrolysis of a higher molecular weight PLG copolymer material, by dissolving the starting copolymer material, which is not a product of hydrolysis of a higher molecular weight PLG copolymer material, in a solvent, then precipitating the inventive low-burst copolymer material with a non-solvent. This process, as applied to a starting material that has never been subjected to hydrolysis, separates out an amount of the removed copolymer fraction effective to confer desirable controlled release properties including low initial burst upon the copolymer of the invention.

The type, molecular weight, and amount of the preferred biodegradable thermoplastic polyester present in the flowable composition will typically depend upon the desired properties of the controlled sustained release implant. For example, the type, molecular weight, and amount of biodegradable thermoplastic polyester can influence the length of time in which the rapamycin or rapamycin derivative is released from the controlled sustained release implant. Specifically, in one embodiment of the present invention, the composition can be used to formulate a one month sustained release delivery system of rapamycin. In such an embodiment, the biodegradable thermoplastic polyester can be a 50/50, 65/35, 55/45, 75/25, 85/15, 90/10, or 95/5 poly(DL-lactide-co-glycolide) having a carboxy terminal group, preferably a 65/35 poly(DL-lactide-co-glycolide) having a carboxy terminal group; can be present in about 20 wt. % to about 70 wt. % of the composition; and can have an average molecular weight of about 15,000 to about 45,000, about 23,000 to about 45,000, or about 20,000 to about 40,000.

In another embodiment of the present invention, a flowable composition as described herein can be formulated to provide a three month sustained release delivery system of rapamycin. In such an embodiment, the biodegradable thermoplastic polyester can be a 50/50, 55/45, 65/35, 75/25, 85/15, 90/10, or 95/5 poly(DL-lactide-co-glycolide) having a carboxy terminal group, preferably a 65/35 or 85/15 poly(DL-lactide-co-glycolide) having a carboxy terminal group; can be present in about 20 wt. % to about 70 wt. % of the composition; and can have an average molecular weight of about 10,000 to about 45,000, about 23,000 to about 45,000, or about 20,000 to about 40,000. In another embodiment, the biodegradable thermoplastic polyester can be an 65/15 poly(DL-lactide-co-glycolide) containing a 1,6-hexane diol chain extender, at a weight percentage of about 20 wt. % to about 70 wt. % of the flowable composition and at an average molecular weight of about 15,000 to about 30,000. Any polyester that has a terminal carboxyl group can optionally be extended with a diol moiety.

In another embodiment of the present invention, the composition can be used to formulate a six month sustained release delivery system of rapamycin. In such an embodiment, the biodegradable thermoplastic polyester can be a 50/50, 55/45, 65/35, 75/25, 85/15, 90/10, or 95/5 poly(DL-lactide-co-glycolide) having a carboxy terminal group, preferably a 50/50 or an 85/15 poly (DL-lactide-co-glycolide) having a carboxy terminal group; can be present in about 20 wt. % to about 70 wt. % of the composition; and can have an average molecular weight of about 10,000 to about 45,000, about 23,000 to about 45,000, or about 20,000 to about 40,000.

Polar Aprotic Organic Solvent

Organic liquids suitable for use in a flowable composition described herein are biocompatible and display a range of solubilities in aqueous medium, body fluid, or water. That range includes complete insolubility at all concentrations upon initial contact, to complete solubility at all concentrations upon initial contact between the organic liquid and the aqueous medium, body fluid or water.

While the solubility or insolubility of the organic liquid in water can be used as a solubility guide according to the invention, its water solubility or insolubility in body fluid typically will vary from its solubility or insolubility in water. Relative to water, body fluid contains physiologic salts, lipids, proteins and the like, and will have a differing solvating ability for organic liquids. This phenomenon is similar to the classic "salting out" characteristic displayed by saline relative to water. Body fluid displays similar variability relative to water but in contrast to a "salting out" factor, body fluid typically has a higher solvating ability for most organic liquids than does water. This higher ability is due in part to the greater lipophilic character of body fluid relative to water, and also in part to the dynamic character of body fluid. In a living organism, body fluid is not static but rather moves throughout the organism. In addition, body fluid is purged or cleansed by tissues of the organism so that body fluid contents are removed. As a result, body fluid in living tissue will remove, solvate or dissipate organic liquids that are utterly insoluble in water.

Pursuant to the foregoing understanding of the solubility differences among water, aqueous media and body fluid, the organic liquid used in the present invention may be completely insoluble to completely soluble in water when the two are initially combined. Preferably the organic liquid is at least slightly soluble, more preferably moderately soluble, especially more preferably highly soluble, and most preferably soluble at all concentrations in water. The corresponding solubilities of the organic liquids in aqueous media and body fluid will tend to track the trends indicated by the water solubilities. In body fluid, the solubilities of the organic liquids will tend to be higher than those in water.

When an organic liquid that is insoluble to only slightly soluble in body fluid is used in any of the embodiments of the sustained release delivery system, it will allow water to permeate into the implanted delivery system over a period of time ranging from seconds to weeks or months. This process may decrease or increase the delivery rate of the rapamycin and in the case of the flowable composition, it will affect the rate of coagulation or solidification. When an organic liquid that is moderately soluble to very soluble in body fluid is used in any of the embodiments of the delivery system, it will diffuse into body fluid over a period of minutes to days. The diffusion rate may decrease or increase the delivery rate of the rapamycin or rapamycin derivative. When highly soluble organic liquids are used, they will diffuse from the delivery system over a period of seconds to hours. Under some circumstances, this rapid diffusion is responsible at least in part for the so-called burst effect. The burst effect is a short-lived but rapid release of rapamycin or a rapamycin derivative upon implantation of the delivery system followed by a long-lived, slow release of rapamycin.

Organic liquids used in the delivery system of the present invention include aliphatic, aryl, and arylalkyl; linear, cyclic and branched organic compounds that are liquid or at least flowable at ambient and physiological temperature and contain such functional groups as alcohols, alkoxylated alcohols, ketones, ethers, polymeric ethers, amides, esters, carbonates, sulfoxides, sulfones, any other functional group that is compatible with living tissue, and any combination thereof. The organic liquid preferably is a polar aprotic or polar protic organic solvent. Preferably, the organic liquid has a molecular weight in the range of about 30 to about 1000.

Preferred biocompatible organic liquids that are at least slightly soluble in aqueous or body fluid include N-methyl-2-pyrrolidone, 2-pyrrolidone; $C_1$ to $C_{15}$ alcohols, diols, triols and tetraols such as ethanol, glycerine, propylene glycol, butanol; $C_3$ to $C_{15}$ alkyl ketones such as acetone, diethyl ketone and methyl ethyl ketone; $C_3$ to $C_{15}$ esters and alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, and glyceryl triacetate; $C_1$ to $C_{15}$ amides such as dimethylformamide, dimethylacetamide and caprolactam; $C_3$ to $C_{20}$ ethers such as tetrahydrofuran, or solketal; tweens, triacetin, decylmethylsulfoxide, dimethyl sulfoxide, oleic acid, 1-dodecylazacycloheptan-2-one, N-methyl-2-pyrrolidone, esters of carbonic acid and alkyl alcohols such as propylene carbonate, ethylene carbonate, and dimethyl carbonate; alkyl ketones such as acetone and methyl ethyl ketone; alcohols such as solketal, glycerol formal, and glycofurol; dialkylamides such as dimethylformamide, dimethylacetamide, dimethylsulfoxide, and dimethylsulfone; lactones such as epsilon-caprolactone and butyrolactone; cyclic alkyl amides such as caprolactam; triacetin and diacetin; aromatic amides such as N,N-dimethyl-m-toluamide, and mixtures and combinations thereof. Preferred solvents include N-methyl-2-pyrrolidone, 2-pyrrolidone, dimethylsulfoxide, ethyl lactate, propylene carbonate, solketal, triacetin, glycerol formal, isopropylidene glycol, and glycofurol.

Other preferred organic liquids are benzyl alcohol, benzyl benzoate, dipropylene glycol, tributyrin, ethyl oleate, glycerin, glycofural, isopropyl myristate, isopropyl palmitate, oleic acid, polyethylene glycol, propylene carbonate, and triethyl citrate. The most preferred solvents are N-methyl-2-pyrrolidone (NMP), 2-pyrrolidone, dimethyl sulfoxide, triacetin, and propylene carbonate because of their solvating ability and their compatibility.

The type and amount of biocompatible organic liquid present in the flowable composition will typically depend on the desired properties of the controlled release implant as described in detail below. Preferably, the flowable composition includes about 0.001 wt % to about 90 wt %, more preferably about 5 wt % to about 70 wt %, most preferably 5 to 60 wt % of an organic liquid.

The solubility of the biodegradable thermoplastic polymers in the various organic liquids will differ depending upon their crystallinity, their hydrophilicity, hydrogen-bonding, and molecular weight. Lower molecular-weight polymers will normally dissolve more readily in the organic liquids than high-molecular-weight polymers. As a result, the concentration of a thermoplastic polymer dissolved in the various organic liquids will differ depending upon type of polymer and its molecular weight. Moreover, the higher molecular-weight thermoplastic polymers will tend to give higher solution viscosities than the low-molecular-weight materials.

When the organic liquid forms part of the flowable composition described herein, it functions not only to enable easy, non-surgical placement of the sustained release delivery system into living tissue. It also facilitates transformation of the flowable composition to an in situ formed implant. Although it is not meant as a limitation of the invention, it is believed that the transformation of the flowable composition is the result of the dissipation of the organic liquid from the flowable composition into the surrounding body fluid and tissue and the infusion of body fluid from the surrounding tissue into the flowable composition. It is believed that during this transformation, the thermoplastic polymer and organic liquid within the flowable composition partition into regions rich and poor in polymer.

For a flowable composition described herein, the concentration of the thermoplastic polymer in the organic liquid according to the invention will range from about 0.01 g per mL of organic liquid to a saturated concentration. Typically, the saturated concentration will be in the range of 80 to 95 wt % solids or 4 to almost 5 gm per mL of organic liquid, assuming that the organic liquid weighs approximately 1 gm per mL.

For polymers that tend to coagulate slowly, a solvent mixture can be used to increase the coagulation rate. In essence, one liquid component of the solvent mixture is a good solvent for the polymer, and the other liquid component of the solvent mixture is a poorer solvent or a non-solvent. The two liquids are mixed at a ratio such that the polymer is still soluble but precipitates with the slightest increase in the amount of non-solvent, such as water in a physiological environment. By necessity, the solvent system must be miscible with both the polymer and water. An example of such a binary solvent system is the use of N-methylpyrrolidone and ethanol. The addition of ethanol to the NMP/polymer solution increases its coagulation rate.

For the formed implant of the invention, the presence of the organic liquid can serve to provide the following properties: plasticization, moldability, flexibility, increased or decreased homogeneity, increased or decreased release rate for the rapamycin or rapamycin derivative, leaching, promotion or retardation of body fluid influx into the implant, patient comfort, compatibility of thermoplastic polymer and rapamycin and the like. Generally the concentration of organic liquid in the formed implant may range from about 0.001 wt. % to as much as about 60 wt. %. Generally, the concentration will be less than an amount that would cause reversion of the formed implant into a flowable composition. Also, the organic liquid may preferentially be chosen so as to display less than substantial ability to dissolve the thermoplastic polymer.

The pliability of the implant can be substantially maintained throughout its life if additives such as the organic liquid are maintained in the implant. Such additives also can act as a plasticizer for the thermoplastic polymer and at least in part may remain in the implant. One such additive having these properties is an organic liquid of low water solubility to water insolubility. Such an organic liquid providing these pliability and plasticizing properties may be included in the delivery system as the sole organic liquid or may be included in addition to an organic liquid that is moderately to highly water soluble.

Organic liquids of low water solubility or water insolubility, such as those forming aqueous solutions of no more than 5% by weight in water, can function as a pliability, plasticizing component and in addition can act as the solvating component for the flowable composition embodiment of the invention. Such organic liquids can act as plasticizers for the thermoplastic polymer. When the organic liquid has these properties, it is a member of a subgroup of organic liquids termed "plasticizer". The plasticizer influences the pliability and moldability of the implant composition such that it is rendered more comfortable to the patient when implanted. Moreover, the plasticizer has an effect upon the rate of sustained release of rapamycin such that the rate can be increased or decreased according to the character of the plasticizer incorporated into the implant composition. In general, the organic liquid acting as a plasticizer is believed to facilitate molecular movement within the solid or gel thermoplastic matrix. The plasticizing capability enables polymer molecules of the matrix to move relative to each other so that pliability and easy moldability are provided. The plasticizing capability also enables easy movement of rapamycin so that in some situations, the rate of sustained release is either positively or negatively affected.

High Water Solubility Organic Liquids

A moderate to highly water soluble organic liquid can be generally used in the flowable composition of the invention, especially when pliability will not be an issue after formation of the implant. Use of the highly water soluble organic liquid will provide an implant having the physical characteristics of an implant made through direct insertion of the flowable composition.

Use of a moderate to highly water soluble organic liquid in a flowable composition described herein will facilitate intimate combination and mixture of the other components therein. It will promote solid or gel homogeneity and pliability of an ex vivo formed implant so that such an implant can be readily inserted into appropriate incisions or trocar placements in tissue.

Useful, highly water soluble organic liquids include, for example, substituted heterocyclic compounds such as N-methyl-2-pyrrolidone (NMP) and 2-pyrrolidone; $C_2$ to $C_{10}$ alkanoic acids such as acetic acid and lactic acid, esters of hydroxy acids such as methyl lactate, ethyl lactate, alkyl citrates and the like; monoesters of polycarboxylic acids such as monomethyl succinate acid, monomethyl citric acid and the like; ether alcohols such as glycofurol, glycerol formal, isopropylidene glycol, 2,2-dimethyl-1,3-dioxolone-4-methanol; Solketal; dialkylamides such as dimethylformamide and dimethylacetamide; dimethylsulfoxide (DMSO) and dimethylsulfone; lactones such as epsilon, caprolactone and butyrolactone; cyclic alkyl amides such as caprolactam; and mixtures and combinations thereof. Preferred organic liquids include N-methyl-2-pyrrolidone, 2-pyrrolidone, dimethylsulfoxide, ethyl lactate, glycofurol, glycerol formal, and isopropylidene glycol.

Low Water Solubility Organic Liquids/Solvents

As described above, an organic liquid of low or no water solubility (hereinafter low/no liquid) may also be used in the sustained release delivery system. Preferably, a low/no liquid is used when it is desirable to have an implant that remains pliable, is to be extrudable is to have an extended release and the like. For example, the release rate of the biologically active agent can be affected under some circumstances through the use of a low/no liquid. Typically such circumstances involve retention of the organic liquid within the implant product and its function as a plasticizer or rate modifier.

Examples of low or nonsoluble organic liquids include esters of carbonic acid and aryl alcohols such as benzyl benzoate; $C_4$ to $C_{10}$ alkyl alcohols; $C_1$ to $C_6$ alkyl $C_2$ to $C_6$ alkanoates; esters of carbonic acid and alkyl alcohols such as propylene carbonate, ethylene carbonate and dimethyl carbonate, alkyl esters of mono-, di-, and tricarboxylic acids, such as 2-ethoxyethyl acetate, ethyl acetate, methyl acetate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate and glyceryl triacetate; alkyl ketones such as methyl ethyl ketone; as well as other carbonyl, ether, carboxylic ester, amide and hydroxy containing liquid organic compounds having some solubility in water. Propylene carbonate, ethyl acetate, triethyl citrate, isopropyl myristate, and glyceryl triacetate are preferred because of biocompatibility and pharmaceutical acceptance.

Additionally, mixtures of the foregoing high and low or no solubility organic liquids providing varying degrees of solubility for the matrix forming material can be used to alter the life time, rate of rapamycin or rapamycin derivative release and other characteristics of the implant. Examples include a combination of N-methylpyrrolidone and propylene carbonate, which provides a more hydrophobic solvent than N-methylpyrrolidone alone, and a combination of N-methylpyrrolidone and polyethylene glycol, which provides a more hydrophilic solvent than N-methylpyrrolidone alone.

The organic liquid for inclusion in the composition should be biocompatible. Biocompatible means that as the organic liquid disperses or diffuses from the composition, it does not result in substantial tissue irritation or necrosis surrounding the implant site.

Organic Liquid for the Preferred Flowable Composition

For the preferred flowable composition incorporating a thermoplastic polyester, any suitable polar aprotic organic liquid can be employed, provided that the suitable polar aprotic solvent displays a body fluid solubility within a range of completely soluble in all proportions to only very slightly soluble. Suitable polar aprotic organic liquids are disclosed, e.g., in *Aldrich Handbook of Fine Chemicals and Laboratory Equipment*, Milwaukee, Wis. (2000); U.S. Pat. Nos. 5,324,519; 4,938,763; 5,702,716; 5,744,153; and 5,990,194. A suitable polar aprotic liquid should be able to diffuse over time into body fluid so that the flowable composition coagulates or solidifies. The diffusion may be rapid or slow. It is also preferred that the polar aprotic liquid for the biodegradable polymer be non-toxic and otherwise biocompatible.

The polar aprotic organic liquid is preferably biocompatible. Examples of suitable polar aprotic organic liquid include those having an amide group, an ester group, a carbonate group, a ketone, an ether, a sulfonyl group, or a combination thereof. Examples are mentioned above.

N-methyl-2-pyrrolidone (NMP) is a known irritant (Jungbauer, 2001; Leira, 1992) that would be expected to cause irritation and inflammation after injection into the sensitive tissues of the eye. Surprisingly, the NMP-containing formulations of the flowable composition described herein are well-tolerated, based on both ocular examination and histopathology. Thus, NMP is a preferred polar aprotic organic liquid for intravitreal or subconjuctival implantation in the flowable composition. In other embodiments, the polar aprotic organic liquid can be 2-pyrrolidone, N,N-dimethylformamide, dimethyl sulfoxide, propylene carbonate, caprolactam, triacetin, or any combination thereof.

The solubility of the biodegradable thermoplastic polyesters in the various polar aprotic liquids will differ depending upon their crystallinity, their hydrophilicity, hydrogen-bonding, and molecular weight. Thus, not all of the biodegradable thermoplastic polyesters will be soluble to the same extent in the same polar aprotic organic liquid, but each biodegradable thermoplastic polymer or copolymer should be soluble in its appropriate polar aprotic solvent. Lower molecular-weight polymers will normally dissolve more readily in the liquids than high-molecular-weight polymers. As a result, the concentration of a polymer dissolved in the various liquids will differ depending upon type of polymer and its molecular weight. Conversely, the higher molecular-weight polymers will normally tend to coagulate or solidify faster than the very low-molecular-weight polymers. Moreover the higher molecular-weight polymers will tend to give higher solution viscosities than the low-molecular-weight materials.

For example, low-molecular-weight polylactic acid formed by the condensation of lactic acid will dissolve in N-methyl-2-pyrrolidone (NMP) to give a 73% by weight solution which still flows easily through a 23-gauge syringe needle, whereas a higher molecular-weight poly(DL-lactide) (DL-PLA) formed by the additional polymerization of DL-lactide gives the same solution viscosity when dissolved in NMP at only 50% by weight. The higher molecular-weight polymer solution coagulates immediately when placed into water. The low-molecular-weight polymer solution, although more concentrated, tends to coagulate very slowly when placed into water.

It has also been found that solutions containing very high concentrations of high molecular weight polymers sometimes coagulate or solidify slower than more dilute solutions. It is believed that the high concentration of polymer impedes the diffusion of solvent from within the polymer matrix and consequently prevents the permeation of water into the matrix where it can precipitate the polymer chains. Thus, there is an optimum concentration at which the solvent can diffuse out of the polymer solution and water penetrates within to coagulate the polymer.

The concentration and species of the polar aprotic organic liquid for the preferred flowable composition of the invention incorporating a thermoplastic polyester will typically depend upon the desired properties of the controlled release implant. For example, the species and amount of biocompatible polar aprotic solvent can influence the length of time in which the rapamycin is released from the controlled release implant. Specifically, in one embodiment of the present invention, the flowable composition can be used to formulate a one month delivery system of rapamycin and its derivatives. In such an embodiment, the biocompatible polar aprotic solvent can preferably be N-methyl-2-pyrrolidone and can preferably present in about 30 wt. % to about 60 wt. % of the composition. Alternatively, in other embodiments of the present invention, the composition can be used to formulate a three month or six month delivery system of rapamycin. In such embodiments, the biocompatible polar aprotic solvent can preferably be N-methyl-2-pyrrolidone and can preferably present in about 20 wt. % to about 60 wt. % of the composition.

Rapamycin

Rapamycin (also known as sirolimus and marketed under the trade name Rapamune®) is a known macrolide. The molecular formula of rapamycin is $C_{51}H_{79}NO_{13}$ and it has the following structure:

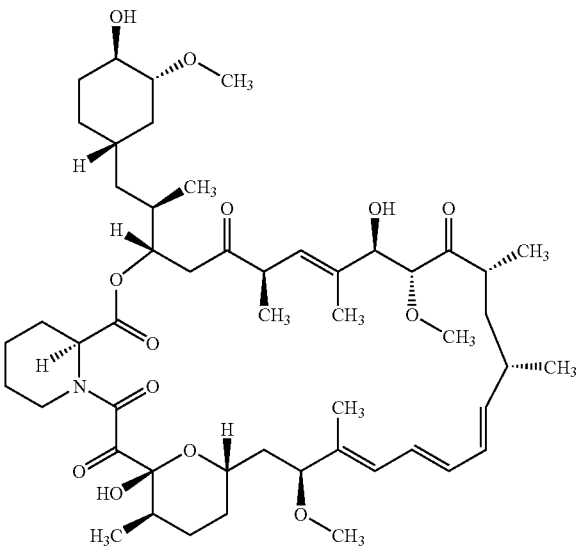

Rapamycin binds to a member of the FK binding protein (FKBP) family, FKBP 12. The rapamycin/FKBP 12 complex binds to the protein kinase mTOR to block the activity of signal transduction pathways. Because the mTOR signaling network includes multiple tumor suppressor genes, including PTEN, LKB1, TSC1, and TSC2, and multiple proto-oncogenes including PI3K, Akt, and eIF4E, mTOR signaling plays a central role in cell survival and proliferation. Binding of the rapamycin/FKBP complex to mTOR causes arrest of the cell cycle in the G1 phase (Janus, A. et al., 2005); thus, rapamycin has been studied and employed in the treatment of various conditions characterized by abnormal or detrimental cell survival and proliferation (see Therapeutic Use section below).

Many rapamycin derivatives have been disclosed. These derivatives include, but are not limited to: rapamycin oximes (U.S. Pat. No. 5,446,048); rapamycin aminoesters (U.S. Pat. No. 5,130,307); rapamycin dialdehydes (U.S. Pat. No. 6,680,330); rapamycin 29-enols (U.S. Pat. No. 6,677,357); O-alkylated rapamycin derivatives (U.S. Pat. No. 6,440,990); water soluble rapamycin esters (U.S. Pat. No. 5,955,457); alkylated rapamycin derivatives (U.S. Pat. No. 5,922,730); rapamycin amidino carbamates (U.S. Pat. No. 5,637,590); biotin esters of rapamycin (U.S. Pat. No. 5,504,091); carbamates of rapamycin (U.S. Pat. No. 5,567,709); rapamycin hydroxyesters (U.S. Pat. No. 5,362,718); rapamycin 42-sulfonates and 42-(N-carbalkoxy)sulfamates (U.S. Pat. No. 5,346,893); rapamycin oxepane isomers (U.S. Pat. No. 5,344,833); imidazolidyl rapamycin derivatives (U.S. Pat. No. 5,310,903); rapamycin alkoxyesters (U.S. Pat. No. 5,233,036); rapamycin pyrazoles (U.S. Pat. No. 5,164,399); acyl derivatives of rapamycin (U.S. Pat. No. 4,316,885); reduction products of rapamycin (U.S. Pat. Nos. 5,102,876 and 5,138,051); rapamycin amide esters (U.S. Pat. No. 5,118,677); rapamycin fluorinated esters (U.S. Pat. No. 5,100,883); rapamycin acetals (U.S. Pat. No. 5,151,413); oxorapamycins (U.S. Pat. No. 6,399,625); and rapamycin silyl ethers (U.S. Pat. No. 5,120,842).

Rapamycin and its derivatives are preferably lyophilized prior to use. Typically, the rapamycin can be dissolved in an aqueous solution, sterile filtered and lyophilized in a syringe. In a separate process, the thermoplastic polymer/organic liquid solution can be filled into second syringe. The two syringes can then be coupled together and the contents can be drawn back and forth between the two syringes until the thermoplastic polymer, organic liquid and the rapamycin or rapamycin derivative are effectively mixed together, forming a flowable composition. The flowable composition can be drawn into one syringe. The two syringes can then be disconnected and a needle attached to the syringe containing the flowable composition. The flowable composition can then be injected through the needle into the body. The flowable composition can be formulated and administered to a patient as described in, e.g., U.S. Pat. Nos. 5,324,519; 4,938,763; 5,702,716; 5,744,153; and 5,990,194; or as described herein. Once administered, the organic liquid dissipates, the remaining polymer gels or solidifies, and a matrix structure is formed. The organic liquid will dissipate and the polymer will solidify or gel so as to entrap or encase the rapamycin within the matrix.

The release of rapamycin or a rapamycin derivative from the implant of the invention will follow the same general rules for release of a drug from a monolithic polymeric device. The release of rapamycin can be affected by the size and shape of the implant, the loading of rapamycin within the implant, the permeability factors involving the rapamycin and the particular polymer, and the degradation of the polymer. Depending upon the amount of rapamycin selected for delivery, the above parameters can be adjusted by one skilled in the art of drug delivery to give the desired rate and duration of release.

The amount of rapamycin or rapamycin derivative incorporated into the sustained release delivery system of the invention depends upon the desired release profile, the concentration of rapamycin required for a biological effect, and the length of time that the rapamycin has to be released for treatment. There is no upper limit on the amount of rapamycin or rapamycin derivative incorporated into the sustained release delivery system except for that of an acceptable solution or dispersion viscosity for injection through a syringe needle. The lower limit of rapamycin incorporated into the sustained release delivery system is dependent upon the activity of the rapamycin and the length of time needed for treatment. Specifically, in one embodiment of the present invention, the sustained release delivery system can be formulated to provide a one month release of rapamycin. In such an embodiment, the rapamycin can preferably be present in about 0.1 wt. % to about 50 wt. %, preferably about 2 wt. % to about 25 wt. % of the composition. Alternatively, in another embodiment of the present invention, the sustained release delivery system can be formulated to provide a three month delivery of rapamycin. In such an embodiment, the rapamycin can preferably be present in about 0.1 wt. % to about 50 wt. %, preferably about 2 wt. % to about 25 wt. % of the composition. Alternatively, in another embodiment of the present invention, the sustained release delivery system can be formulated to provide a six month delivery of rapamycin. In such an embodiment, the rapamycin can preferably be present in about 0.1 wt. % to about 50 wt. %, preferably about 2 wt. % to about 25 wt. % of the composition. The gel or solid implant formed from the flowable composition will release the rapamycin contained within its matrix at a controlled rate until the implant is effectively depleted of rapamycin.

Adjuvants and Carriers

The sustained release delivery system may include a release rate modifier to alter the sustained release rate of rapamycin or rapamycin derivative from the implant matrix. The use of a release rate modifier may either decrease or increase the release of rapamycin in the range of multiple orders of magnitude (e.g., 1 to 10 to 100), preferably up to a ten-fold change, as compared to the release of rapamycin from an implant matrix without the release rate modifier.

With the addition of a hydrophobic release rate modifier such as hydrophobic ethyl heptanoate, to the sustained release delivery system, and formation of the implant matrix through interaction of the flowable composition and body fluid, the release rate of rapamycin or rapamycin derivative can be slowed. Hydrophilic release rate modifiers such as polyethylene glycol may increase the release of the rapamycin. By an appropriate choice of the polymer molecular weight in combination with an effective amount of the release rate modifier, the release rate and extent of release of rapamycin from the implant matrix may be varied, for example, from relatively fast to relatively slow.

Useful release rate modifiers include, for example, organic substances which are water-soluble, water-miscible, or water insoluble (i.e., hydrophilic to hydrophobic).

The release rate modifier is preferably an organic compound which is thought to increase the flexibility and ability of the polymer molecules and other molecules to slide past each other even though the molecules are in the solid or highly viscous state. Such an organic compound preferably includes a hydrophobic and a hydrophilic region. It is preferred that a release rate modifier is compatible with the combination of polymer and organic liquid used to formulate the sustained release delivery system. It is further preferred that the release rate modifier is a pharmaceutically-acceptable substance.

Useful release rate modifiers include, for example, fatty acids, triglycerides, other like hydrophobic compounds, organic liquids, plasticizing compounds and hydrophilic compounds. Suitable release rate modifiers include, for example, esters of mono-, di-, and tricarboxylic acids, such as 2-ethoxyethyl acetate, methyl acetate, ethyl acetate, diethyl phthalate, dimethyl phthalate, dibutyl phthalate, dimethyl adipate, dimethyl succinate, dimethyl oxalate, dimethyl citrate, triethyl citrate, acetyl tributyl citrate, acetyl triethyl citrate, glycerol triacetate, di(n-butyl)sebecate, and the like; polyhydroxy alcohols, such as propylene glycol, polyethylene glycol (PEG), glycerin, sorbitol, and the like; fatty acids; triesters of glycerol, such as triglycerides, epoxidized soybean oil, and other epoxidized vegetable oils; sterols, such as cholesterol; alcohols, such as $C_6$-$C_{12}$ alkanols, 2-ethoxyethanol, and the like. The release rate modifier may be used singly or in combination with other such agents. Suitable combinations of release rate modifiers include, for example, glycerin/propylene glycol, sorbitol/glycerine, ethylene oxide/propylene oxide, butylene glycol/adipic acid, and the like. Preferred release rate modifiers include dimethyl citrate, triethyl citrate, ethyl heptanoate, glycerin, PEG 5000 and hexanediol.

The amount of the release rate modifier included in a flowable composition as described herein will vary according to the desired rate of release of the rapamycin or rapamycin derivative from the implant matrix. Preferably, the sustained release delivery system contains about 0.5-30%, preferably about 5-10%, of a release rate modifier.

Other solid adjuvants may also be optionally combined with the sustained release delivery system to act as carriers, especially isolation carriers. These include additives or excipients such as a starch, sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, and/or polyvinylpyrrolidone.

Additional adjuvants may include oils such as peanut oil, sesame oil, cottonseed oil, corn oil and olive oil as well as esters of fatty acids such as ethyl oleate, isopropyl myristate, fatty acid glycerides and acetylated fatty acid glycerides. Also included are alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum may also be used in the formulations. Pectins, carbomers, methyl cellulose, hydroxypropyl cellulose, hydroxypropyl methyl cellulose or carboxymethyl cellulose may also be included. These compounds can serve as isolation carriers by coating the rapamycin thereby preventing its contact with the organic solvent and other ingredients of the flowable composition. As isolation carriers, these compounds also help lower the burst effect associated with the coagulation of the flowable composition in situ.

Optionally, other compounds such as, but not limited to, stabilizers, antimicrobial agents, antioxidants, pH modifiers, bioavailability modifiers and combinations of these are included. Emulsifiers and surfactants such as fatty acids, or a non-ionic surfactants including natural or synthetic polar oil, fatty acid esters, polyol ethers and mono-, di- or tri-glycerides may also be included.

Implants

The implant formed within the flowable composition as described herein will slowly biodegrade within the body and allow natural tissue to grow and replace the impact as it disappears. The implant formed from the flowable composition will release the drug contained within its matrix at a controlled rate until the drug is depleted. With certain drugs, the polymer will degrade after the drug has been completely released. With other drugs such as peptides or proteins, the drug will be completely released only after the polymer has degraded to a point where the non-diffusing drug has been exposed to the body fluids. The implant can have any suitable shape and can have any suitable form. For example, the implant can be a solid, semi-solid, wax-like, viscous, or the implant can be gelatinous.

The porous structure of the solid matrices, e.g., in situ formed implants, implants, implantable articles, biodegradable articles and devices of the invention, is influenced by nature of the organic solvent and thermoplastic polymer, by their solubility in water, aqueous medium or body fluid (which may differ for each medium) and by the presence of an additional substances (e.g., pore forming moiety). The porous structure is believed to be formed by several mechanisms and their combinations. The dissipation, disbursement or diffusion of the solvent out of the solidifying flowable composition into the adjacent fluids may generate pores, including pore channels, within the polymer matrix. The infusion of aqueous medium, water or body fluid into the flowable composition also occurs and is in part also responsible for creation of pores. Generally, it is believed that the porous structure is formed during the transformation of the flowable composition to an implant, article and the like. During this process, it is believed, as explained above, that the organic solvent and thermoplastic polymer partition within the flowable composition into regions that are rich and poor in thermoplastic polymer. The partition is believed to occur as a result of the dynamic interaction of aqueous infusion and solvent dissipation. The infusion involves movement of aqueous medium, water or body fluid into the flowable composition and the dissipation involves movement of the organic solvent into the medium surrounding the flowable composition. The regions of the flowable composition that are poor in thermoplastic polymer become infused with a mixture of organic solvent and water, aqueous medium or body fluid. These regions are believed to eventually become the porous network of the implant, article and the like.

Typically, the macroscopic structure of the solid matrix involves a core and a skin. Typically, the core and skin are microporous but the skin pores are of smaller size than those of the core unless a separate pore forming agent is used as discussed below. Preferably, the outer skin portion of the solid matrix has pores with diameters significantly smaller in size than these pores in the inner core portion. The pores of the core are preferably substantially uniform and the skin is typically functionally non-porous compared to the porous nature of the core. The size of the pores of the implant, article, device and the like are in the range of about 4-1000 microns, preferably the size of pores of the skin layer are about 1-500 microns. The porosity of such matrices is described by U.S. Pat. No. 5,324,519, the disclosure of which is incorporated herein by reference.

The solid microporous implant, article, device and the like will have a porosity in the range of about 5-95% as measured by the percent solid of the volume of the solid. The development of the degree of porosity will be governed at least in part by the degree of water solubility of the organic solvent and thermoplastic polymer. If the water solubility of the organic solvent is high and that of the polymer is extremely low or non-existent, a substantial degree of porosity will be developed, typically on the order of 30 to 95%. If the organic solvent has a low water solubility and the polymer has a low to non-existent water solubility, a low degree of porosity will be developed, typically on the order of 5 to 40%. It is believed that the degree of porosity is in part controlled by the polymer-solvent partition when the flowable composition contacts an aqueous medium and the like. The control of the degree of porosity is beneficial for generation of differing kinds of biodegradable articles, implants and devices according to the invention. For example, if strength is a requirement for the article, implant or device and the like, it may be beneficial to have a low degree of porosity.

The flowable composition can be administered to form the implant by a variety of methods, including subconjuctival and intravitreal injection. These injections can be administered against the outside of the eye and through the sclera (the tough outer membrane) of the eye into the vitreous. The implant would be expected either to float in the aqueous environment of the humor or to form multiple, floating particles. Surprisingly, this does not occur. Intravitreal injections allow the puncture hole to self-seal with the ATRIGEL® formulations when the needle is removed from the eye. The implant is thus affixed to the sclera and forms a plug to prevent loss of vitreous humor. Similarly, the subconjuctivally and sub-Tenons injected implants adhere to the outer surface of the eye due to the tackiness of the ATRIGEL® implant. Thus, the retina is not blocked or hindered from receiving light, because the implant is not floating in the vitreous humor.

Pore Forming Agent/Additive

The flowable composition of the present invention can be used for implantation, injection, or otherwise placed totally or partially within the body. The rapamycin or rapamycin derivative of the composition and the polymer of the invention may form a homogeneous matrix, or the rapamycin or rapamycin derivative may be encapsulated in some way within the polymer. For example, the rapamycin may be first encapsulated in a microsphere and then combined with the polymer in such a way that at least a portion of the microsphere structure is maintained. Alternatively, the rapamycin may be sufficiently immiscible in the polymer of the invention that it is dispersed as small droplets, rather than being dissolved, in the polymer. Either form is acceptable, but it is preferred that, regardless of the homogeneity of the composition, the release rate of rapamycin in vivo remains controlled, at least partially as a function of hydrolysis of the ester bond of the polymer upon biodegradation.

Additives can be used to advantage in further controlling the pore size in the solid matrix, which influences the structure of the matrix and the release rate of the rapamycin or the diffusion rate of body fluids. For example, if the flowable composition is too impervious to aqueous medium, water or tissue ingrowth, a pore-forming agent can be added to generate additional pores in the matrix. Any biocompatible water-soluble material can be used as the pore-forming additive. These additives can be either soluble in the flowable composition or simply dispersed within it. They are capable of dissolving, diffusing or dispersing out of both the coagulating polymer matrix whereupon pores and microporous channels are generated. The amount of pore-forming additive (and size of dispersed particles of such pore-forming agent, if appropriate) within the flowable composition will directly affect the size and number of the pores in the polymer matrix.

Pore-forming additives include any acceptable organic or inorganic substance that is substantially miscible in water and body fluids and will dissipate from the forming and formed matrix into aqueous medium or body fluids or water-immiscible substances that rapidly degrade to water soluble substances. It is further preferred that the pore-forming additive is miscible or dispersible in the organic solvent to form a uniform mixture. Suitable pore-forming agents include, for example, sugars such as sucrose and dextrose, salts such as sodium chloride and sodium carbonate, and polymers such as hydroxylpropylcellulose, carboxymethylcellulose, polyethylene glycol, and polyvinylpyrrolidone. The size and extent of the pores can be varied over a wide range by changing the molecular weight and percentage of pore-forming additive incorporated into the flowable composition.

As indicated, upon contact with body fluid, the solvent and optional pore-forming additive dissipate into surrounding tissue fluids. This causes the formation of microporous channels within the coagulating polymer matrix. Optionally, the pore-forming additive may dissipate from the matrix into the surrounding tissue fluids at a rate slower than that of the solvent, or be released from the matrix over time by biodegradation or bioerosion of the matrix. Preferably, the pore-forming additive dissipates from the coagulating implant matrix within a short time following implantation such that a matrix is formed with a porosity and pore structure effective to perform the particular purpose of the implant, as for example, a barrier system for a tissue regeneration site, a matrix for timed-release of a drug or medicament, and the like.

Porosity of the solid polymer matrix may be varied by the concentration of water-soluble or water-miscible ingredients, such as the solvent and/or pore-forming agent, in the polymer composition. For example, a high concentration of water-soluble substances in the flowable composition may produce a polymer matrix having a high degree of porosity. The concentration of the pore-forming agent relative to polymer in the composition may be varied to achieve different degrees of pore-formation, or porosity, in the matrix. Generally, the polymer composition will include about 0.01-1 gram of pore-forming agent per gram polymer.

The size or diameter of the pores formed in the matrix of the implant may be modified according to the size and/or distribution of the pore-forming agent within the polymer matrix. For example, pore-forming agents that are relatively insoluble in the polymer mixture may be selectively included in the polymer composition according to particle size in order to generate pores having a diameter that corresponds to the size of the pore-forming agent. Pore-forming agents that are soluble in the polymer mixture may be used to vary the pore size and porosity of the implant matrix by the pattern of distribution and/or aggregation of the pore-forming agent within the polymer mixture and coagulating and solid polymer matrix.

Pore diameter and distribution within the polymer matrix of the implant may be measured, as for example, according to scanning electron microscopy methods by examination of cross-sections of the polymer matrix. Porosity of the polymer matrix may be measured according to suitable methods known in the art, as for example, mercury intrusion porosimetry, specific gravity or density comparisons, calculation from scanning electron microscopy photographs, and the like. Additionally, porosity may be calculated according to the proportion or percent of water-soluble material included in the polymer composition. For example, a polymer composition which contains about 30% polymer and about 70% solvent and/or other water-soluble components will generate an implant having a polymer matrix of about 70% porosity.

Solid Biodegradable Articles

Microcapsules and microparticles can be formed by techniques known in the art. Briefly, the microcapsule preparation involves formation of an emulsion of rapamycin-carrier micelles in the flowable composition where the carrier is a nonsolvent for the biocompatible, biodegradable, branched thermoplastic polymer of the invention. The micelles are filtered and then suspended in an aqueous medium. The coating of flowable composition on the surfaces of the micelles then solidifies to form the porous microcapsules. Microparticles are formed in a similar process. A mixture of the flowable composition is added dropwise by spraying, dripping, aerosolizing or by other similar techniques to a nonsolvent for the flowable composition. The size and shape of the droplets is controlled to produce the desired shape and size of the porous microparticles. Sheets, membranes and films can be produced by casting the flowable composition onto a suitable nonsolvent and allowing the transformation to take place. Similarly, the viscosity of the flowable composition can be adjusted so that when sprayed or aerosolized, strings rather than droplets are formed. These strings can be cast upon a nonsolvent for the flowable composition such that a filamentous scaffold or membrane is produced. Also, suture material or other similar material can be formed by extrusion of the flowable composition into a non-solvent bath. The extrusion orifice will control the size and shape of the extruded product. The techniques for formation of these ex vivo solid matrices are described in U.S. Pat. Nos. 4,652,441; 4,917,893; 4,954,298; 5,061,492; 5,330,767; 5,476,663; 5,575,987; 5,480,656; 5,643,607; 5,631,020; 5,631,021; 5,651,990, the disclosures of which are incorporated herein by reference with the proviso that the polymers used are the biocompatible, biodegradable, thermoplastic polymers disclosed herein.

These ex vivo solid matrices can be used according to their known functions. Additionally, the implants and other solid articles are can be inserted in a body using techniques known to the art such as through an incision or by trocar.

Absorption Altering Agent

Any suitable and appropriate absorption altering agent can be employed in the flowable composition as described herein. For example, the absorption altering agent can be selected from the group of propylene glycol, glycerol, urea, diethyl sebecate sodium, lauryl sulfate, sodium lauryl sulfate, sorbitan ethoxylates, oleic acid, pyrrolidone carboxylate esters, N-methylpyrrolidone, N,N-diethyl-m-tolumide, dimethyl sulfoxide, alkyl methyl sulfoxides, and combinations thereof.

Therapeutic Use

The use of rapamycin and its derivatives to treat numerous diseases and indications has been disclosed in scientific articles and U.S. patents. The following U.S. patents disclose various properties and uses of rapamycin and are herein incorporated by reference. U.S. Pat. No. 5,100,899 discloses inhibition of transplant rejection by rapamycin; U.S. Pat. No. 3,993,749 discloses rapamycin antifungal properties; U.S. Pat. No. 4,885,171 discloses antitumor activity of rapamycin against lymphatic leukemia, colon and mammary cancers, melanocarcinoma and ependymoblastoma; U.S. Pat. No. 5,206,018 discloses rapamycin treatment of malignant mammary and skin carcinomas, and central nervous system neoplasms; U.S. Pat. No. 4,401,653 discloses the use of rapamycin in combination with picibanil in the treatment of tumors; U.S. Pat. No. 5,078,999 discloses a method of treating systemic lupus erythematosus with rapamycin; U.S. Pat. No. 5,080,899 discloses a method of treating pulmonary inflammation with rapamycin that is useful in the symptomatic relief of diseases in which pulmonary inflammation is a component, i.e., asthma, chronic obstructive pulmonary disease, emphysema, bronchitis, and acute respiratory distress syndrome; U.S. Pat. No. 6,670,355 discloses the use of rapamycin in treating cardiovascular, cerebral vascular, or peripheral vascular disease; U.S. Pat. No. 5,561,138 discloses the use of rapamycin in treating immune related anemia; U.S. Pat. No. 5,288,711 discloses a method of preventing or treating hyperproliferative vascular disease including intimal smooth muscle cell hyperplasia, restenosis, and vascular occlusion with rapamycin; and U.S. Pat. No. 5,321,009 discloses the use of rapamycin in treating insulin dependent diabetes mellitus.

In general, any disease which may be ameliorated, treated, cured or prevented by administration of rapamycin or a rapamycin derivative may be treated by administration of a flowable composition as described herein. The following specific malconditions are exemplary of such diseases. These may all be treated by appropriate, effective administration of a flowable composition formulated to deliver an effective amount of rapamycin or rapamycin derivative. These malconditions include:

a. Organ or tissue transplant rejection, e.g. for the treatment of recipients of e.g. heart, lung, combined heart-lung, liver, kidney, pancreatic, skin or corneal transplants. Also graft-versus-host disease, such as following bone marrow transplantation;

b. Autoimmune disease and inflammatory conditions, in particular inflammatory conditions with an etiology including an autoimmune component such as arthritis (for example rheumatoid arthritis, arthritis chronica progrediente and arthritis deformans) and rheumatic diseases. Specific autoimmune diseases which may be treated by a flowable composition as described herein include, but are not limited to, autoimmune hematological disorders (including e.g. autoimmune lymphoproliferative syndrome, hemolytic anaemia, aplastic anaemia, pure red cell anaemia and idiopathic thrombocytopenia), systemic lupus erythematosus, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease), endocrine opthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, glomerulonephritis (with and without nephrotic syndrome, e.g. including idiopathic nephrotic syndrome or minimal change nephropathy), autosomal-dominant polycystic kidney disease, juvenile dermatomyositis, asthma, chronic obstructive pulmonary disease, emphysema, bronchitis, and acute respiratory distress syndrome;

c. Tumors, hyperproliferative skin disorders and the like;

d. Fungal infections;

e. Dry eye;

f. Vascular disease; and g. Diabetes.

Rapamycin has efficacy in treatment of ocular conditions. U.S. Patent Application Pub. No. 2005/0187241 recites a method for treating an angiogenesis-mediated condition of the retina or choroid by administering rapamycin. U.S. Patent Application Pub. No. 2005/0064010 recites a method for treating wet age-related macular degeneration, comprising administering an effective amount of rapamycin transsclerally.

Examples of neovascular proliferative eye diseases that may be treated by a flowable composition as described herein include:

a. Retinal neovascularization in patients with proliferative or non-proliferative diabetic retinopathy (with or without associated macular edema; with or without pre-retinal hemorrhage; with or without retinal detachment);

b. Choroidal neovascularization in patients with the wet form of age-related macular degeneration (with or without macular edema; with or without hemorrhage; with or without retinal detachment);

c. Choroidal neovascularization in patients with ocular and systemic diseases other than age-related macular degeneration including, but not limited to: pathologic myopia, angioid streaks, presumed ocular histoplasmosis syndrome (POHS), serous chorioiditis, optic head drusen, idiopathic central serous chorioretinopathy, retinal coloboma, Best's disease, retinitis pigmentosa with exudates, serpiginous choroiditis, Behcet's syndrome, chronic uveitis, acute multifocal posterior placoid pigment epitheliopathy, birdshot chorioretinopathy, choroidal rupture, ischemic optic neuropathy, chronic retinal detachment, other conditions of the posterior segment of the eye; and d. Corneal neovascularization.

Examples of other types of proliferative diseases in or near the eye that may be treated by a flowable composition as described herein include:

a. Fibroblastic proliferations including proliferative vitreoretinopathy or pterygium;
b. Autoimmune and inflammatory conditions including Graves' ophthamopathy with periocular and/or intraocular lymphocytic proliferation;
c. Optic neuritis, any type of uveitis, iridocyclitis or scleritis caused by lymphocytic or monocytic cell proliferation;
d. Hematolymphoid neoplasms including intraocular lymphoma and leukemia; and
e. Neoplasia including retinoblastoma, orbital lymphoma, eyelid carcinoma, melanoma, rhabdomyosarcoma, embryonal sarcoma, metastatic malignant tumors or any other benign intraocular tumor, and any oncogenic neovascularization of the eye.

Diabetic eye diseases that may be treated by a flowable composition as described herein include:

a. Non-proliferative retinopathy;
b. Early proliferative, non-high risk, retinopathy;
c. Proliferative retinopathy;
d. Severe retinopathy in patients who have failed photocoagulation; and
e. Diabetic macular edema, including cystoid macular edema.

Examples of inflammation of the eye that can be treated by a flowable composition as described herein include:

a. Non-proliferative diabetic retinopathy;
b. Uveitis; and
c. Inflammation after ocular surgery or injury.

A flowable composition as described herein can be used to treat ocular conditions as a stand-alone therapy, as well as in combination with other treatments. A flowable composition as described herein may be used in combination with:

a. Photodynamic therapy including verteporfin (Visudyne®, QLT, Inc.) and SnET2 (tin etiopurpurin, Miravant, Inc.);
b. Locally injected anti-angiogenic agents, including but not limited to, intravitreal or subconjunctival anti-VEGF agents including but not limited to: Macuge®n (Eyetech Pharmaceuticals, Inc.), Lucentis® or Avastin®, both antibodies against VEGF (Genentech, Inc.), and VEGF Trap (Regeneron Pharmaceuticals, Inc.);
c. Locally injected angiostatic steroids including but not limited to anecortave acetate Retanne™ (Alcon) which are administered as a sub-Tenon injection, or any corticosteroid that is administered locally to the ocular tissues (e.g. triamcinolone); and
d. Systemic therapies for ocular neovascularization, such as squalamine (Genaera, Inc.), siRNAs, and other systemically administered anti-angiogenic agents (e.g. Avastin®).

Dosages

The flowable composition can be formulated for administration less than about once per day. More specifically, the flowable composition can be formulated for administration less than about once per week, less than about once per month, more than about once per year, about once per week to about once per year, or about once per month to about once per year.

The flowable composition will effectively deliver the rapamycin or derivative thereof to mammalian tissue at a suitable, effective, safe, and appropriate dosage. The amount of flowable composition administered will typically depend upon the desired properties of the controlled release implant. For example, the amount of flowable composition can influence the length of time in which the rapamycin or rapamycin derivative is released from the controlled release implant.

The rapamycin or derivative thereof can be released from the controlled-release implant in any suitable manner. For example, the rapamycin or derivative thereof can be released from the controlled-release implant with zero order or first order kinetics. Additionally, the rapamycin or derivative thereof can be released from the controlled-release implant with an acceptable level of drug burst.

Specifically, in one embodiment of the present invention, the composition can be used to formulate a delivery system one month, 1.5 month, 2 month, 3 month, 4 month, 5 month, 6 month or longer period delivery system of rapamycin. In such an embodiment, about 0.001 mL to about 0.5 mL of the flowable composition can be administered, depending on the site of administration. For intravitreal administration, preferably the volume administered is in the range of about 0.001 mL to about 0.10 mL, more preferably between 0.01 mL and 0.05 mL. For subtenon or subconjunctival administration, preferably the volume administered is in the range of 0.01 mL to 0.25 mL. For systemic administration, preferably the volume adminstered is preferably about 0.2 to 2.0 mL, more preferably about 0.5 to 1 mL.

The amount of rapamycin or rapamycin derivative within the flowable composition and the resulting implant will depend upon the disease to be treated, the length of duration desired and the bioavailability profile of the implant, and the site of administration. Generally, the effective amount will be within the discretion and wisdom of the patient's attending physician. Guidelines for administration include dose ranges of from about 0.01 mg to about 200 mg of rapamycin as applied for proliferative and non-proliferative eye diseases. The typical flowable composition effective for such sustained delivery over a 1 to 1.5 month period will preferably contain from about 0.1 mg to about 5 mg of rapamycin per ml of total volume of flowable composition, preferably about 0.5 mg to about 2.5 mg. The typical flowable composition effective for such sustained delivery over a 3 month period will preferably contain from about 0.2 to about 5 mg of rapamycin per ml of total volume of flowable composition, more preferably about 1 mg to about 5 mg. The typical flowable composition effective for such sustained delivery of a 6 month period will contain from about 2 mg to about 10 mg of rapamycin per ml of total volume of flowable composition. The injection volumes for sustained release formulations of the durations noted above preferably range from 0.001 to 0.25 mL per implant, for localized ocular or periocular administration, with smaller volumes of about 0.005 to 0.050 mL generally favored for intravitreal administration. The choice of polymer and the amount of polymer in the formulation will be the primary factor for obtaining the longer sustained release, as discussed above.

All publications, patents, and patent documents are incorporated by reference herein, as though individually incorporated by reference. The invention will now be illustrated with the following non-limiting examples.

The following Examples employ the ATRIGEL® formulation of poly(lactide-coglycolide) and N-methylpyrrolidone in combination with rapamycin as the flowable composition.

EXAMPLES

In the following Examples, ATRIGEL®/Rapamycin refers to ATRIGEL®/Rapamycin formulations; ATRIGEL® is a registered Trademark of QLT USA, Inc. Fort Collins, Colo. The particular form of ATRIGEL® composition used in these examples is provided with the examples. Unless otherwise indicated, the ATRIGEL® product is the thermoplastic polymer poly(lactide-coglycolide) (PLGH) or the thermoplastic polymer poly(lactide-coglycolide extended with 1,6-hexane diol) (PLG) in the organic solvent N-methyl-2-pyrrolidone.

Example 1

Subcutaneous Release from Rapamycin/ATRIGEL® Formulations

Materials and Methods

In this study, ATRIGEL® formulations were tested in male Sprague Dawley Rats. On Day 0, while under general isoflurane anesthesia, each rat was placed in sternal recumbency, its DT region shaved, and the injection site wiped with isopropanol. Each animal was administered a single 100 μL subcutaneous injection of appropriate test article in the dorsal thoracic region. At the appropriate time points, the rats were euthanized with $CO_2$. Test sites were dissected and evaluated for macroscopic tissue reactions immediately following euthanasia. Implants were removed at appropriate time points and precipitation characteristics documented. Representative photographs were taken of the test sites and implants. Injection sites were evaluated for any abnormalities including redness, bleeding, swelling, discharge, bruising, and test article extrusion. Additionally, animals were observed post-administration for signs of overt toxicity.

Preparation of ATRIGEL® Polymer Solutions

Five grams of polymer stock solutions were prepared by weighing a known amount of each polymer solid into individual 20 mL scintillation vials. A known amount of N-methyl-2-pyrrolidone (NMP) was added to each polymer and the mixture placed on ajar mill. The vials were mixed at least 24 hours to create a visually clear solution. Following dissolution of the polymer the vials were sterilized by gamma irradiation at 19.8-22.6 kGy.

Preparation of Rapamycin/ATRIGEL® Formulations

The preparation of the A/B syringe configuration was done as follows: to 1.2 mL female syringes approximately 980 mg of sterilized ATRIGEL® polymer solutions was added. Then, in 1.2 mL male syringes, the appropriate approximate weights of rapamycin were added. Prior to injection the two syringes were coupled and mixed 90 cycles to afford the particular weight % formulations.

Test Article Identification

The following formulations were used in this study:
2% rapamycin in 50% 65/35 PLGH (InV 0.26), and 50% NMP;
2% rapamycin in 50% 75/25 PLGH and 50% NMP;
2% rapamycin in 50% 85/15 PLGH (InV 0.27), and 50% NMP; and
2% rapamycin in 50% 85/15 PLG (InV 0.28), and 50% NMP.

Implant Extraction Procedure

After removal, implants were placed in a −86° C. freezer for at least 1 hour. The frozen samples were then lyophilized for at least 4 hours (often overnight), and minced with scissors until powder-like. The scissors were cleaned after each sample to minimize cross-contamination. Five mL of acetonitrile was then added to each sample. The samples were mixed for at least 4 hours (often overnight) at 200 rpm, 25° C. on an orbital shaker. Three mL of 1:1 Acetonitrile/$H_2O$ was then added to the samples and samples were vortexed. 1.5 mL of the extract was drawn into a 3 mL lure lock syringe and filtered through a 0.2 μm pore size nylon filter into a clean HPLC vial. The solution was finally analyzed by RP-HPLC to determine amounts of rapamycin.

HPLC Procedure

Mobile Phase: 70/30 $CH_3CN/H_2O$

HPLC was conducted using a Phenomenex Luna C18, 5 μm, 4.6×150 mm column that was stored in 50/50 $CH_3CN/H_2O$. The flow rate was 1.5 ml/min and the column temperature was 50° C. Detection was performed at 277 nm (UV) and the total run time was 12 minutes. The injection volume was between 20 and 100 μL. The approximate retention time of rapamycin was 5.5 minutes, and the approximate retention time of rapamycin Species 1: was 6.0 minutes. Note: The amount of rapamycin in test samples was determined from the peak area.

Mean and standard deviation calculations were performed for each test group.

The rapamycin standard was prepared by weighing 5 mg of rapamycin on a microbalance and adding to a 100 mL volumetric flask. The volume was diluted with 70/30 $CH_3CN/H_2O$.

Results

FIG. 1 is a graphical representation of the subcutaneous rapamycin release from the various Rapamycin/ATRIGEL® formulations over a 90-day time period. The 24-hr release of Rapamycin from ATRIGEL® is quite low. The release was found to be controlled by the polymer degradation rate and not diffusion. The formulation containing the 85/15 PLG polymer had a release profile consistent with a 6 month duration of release, having released just under 50% of the rapamycin in the initial 3 month period.

Example 2

Comparison of Rapamycin Release From Different Injection Volumes

Materials and Methods are identical to those described in Example 1 above, except the test article formulations and volumes injected are as follows.

Test Articles

The following formulations and injection volumes were employed in this study:
5% Rapamycin in 50% 65/35 PLGH 0.26 and 50% NMP (10 μL injected, containing 0.5 mg rapamycin);
10% Rapamycin in 50% 65/35 PLGH 0.26 and 50% NMP (10 μL injected, containing 1 mg rapamycin); and
2% Rapamycin in 50% 65/35 PLGH 0.26 and 50% NMP (100 μL injected containing 2 mg rapamycin).

Results

Figure 2:
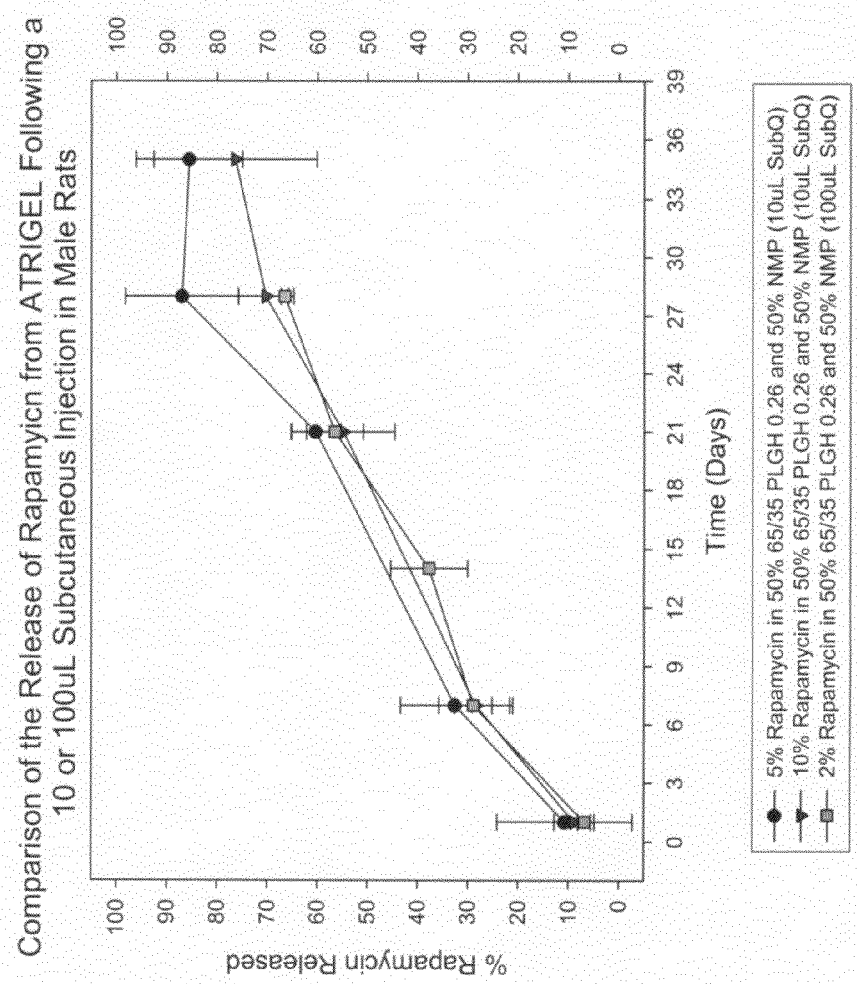
FIG. 2 is a comparison of the rapamycin release after subcutaneous injection of different volumes of rapamycin formulations. Ten µL and 100 µL demonstrate similar release.

FIG. 2 is a graphical representation of the rapamycin release from the three different formulations at injection volumes of either 10 μL or 100 μL. Implants were extracted from the rat subcutaneous injection sites at the time points indicated on the x-axis. HPLC was subsequently performed. Surprisingly, a similar release rate was observed for 10 μL (10%

Rapamycin) and 100 μL (2% Rapamycin) injection volume formulations. Increasing rapamycin load from 5% to 10% slightly increased the release rate. However, overall, volume and rapamycin dose did not significantly impact the release rate in this model.

Example 3

Intravitreal Administration of Rapamycin Atrigel®

Materials and Methods

Ten microliters of the following formulations (prepared as described in Example 1) were administered to Dutch Belted Rabbits by intravitreal injection:

Group I: 5% Rapamycin in 50% 65/35 PLGH 0.26 InV and 50% NMP;
Group II: 10% Rapamycin in 50% 65/35 PLGH 0.26 InV and 50% NMP;
Group III: 10% Rapamycin in 50% 75/25 PLGH 13 kDa and 50% NMP;
Group IV: 10% Rapamycin in 50% 85/15 PLGH 25 kDa and 50% NMP; and
Group V: 10% Rapamycin in 50% 85/15 PLG 25 kDa and 50% NMP.

At Days 2, 15, 22, 29 and 45 post-dosing, ophthalmic examination, intraocular pressure, and histopathology assessments were conducted. Implant extraction and HPLC were conducted as described in Example 1.

Results

Figure 3:
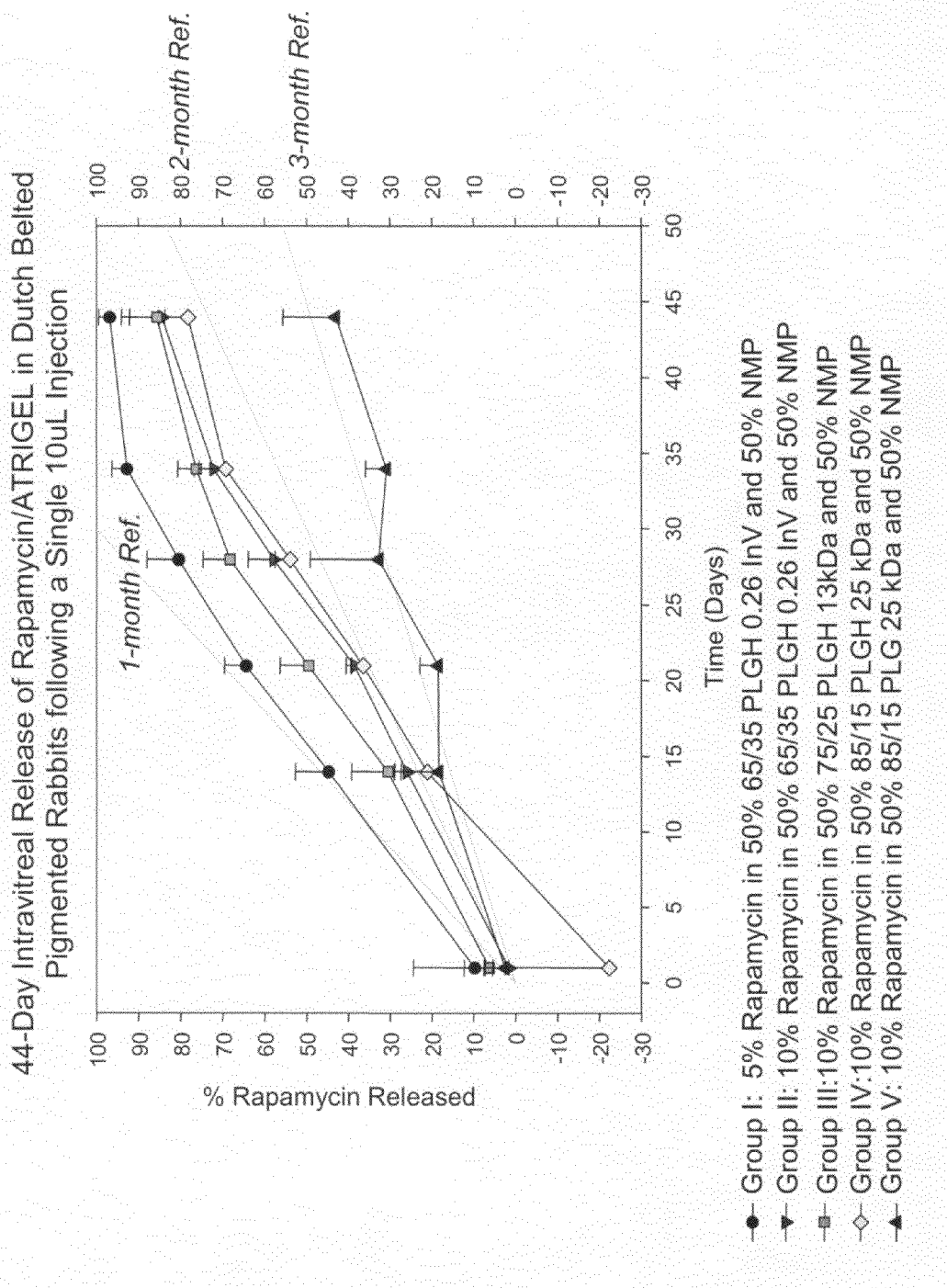
FIG. 3 is a graphical representation of rapamycin release of various formulations administered intravitreally over a 45 day period. The release is linear and continues for over 1 month.

FIG. 3 is a graphical representation of the rapamycin release over the 45 day post-dosing period. All of the formulations exhibit a very linear release, with the 5% rapamycin formulation showing quicker release than the 10% formulations. These data also show that sustained release for more than one month after intravitreal injection is achievable. As expected, the formulation with PLG polymers (without a terminal carboxyl group) provided slower release of rapamycin with PLGH polymers. Increasing the percent lactide from 50/50 to 75/25 or 85/15 tended to slow the release rate (groups II, III, and IV).

Figure 4:
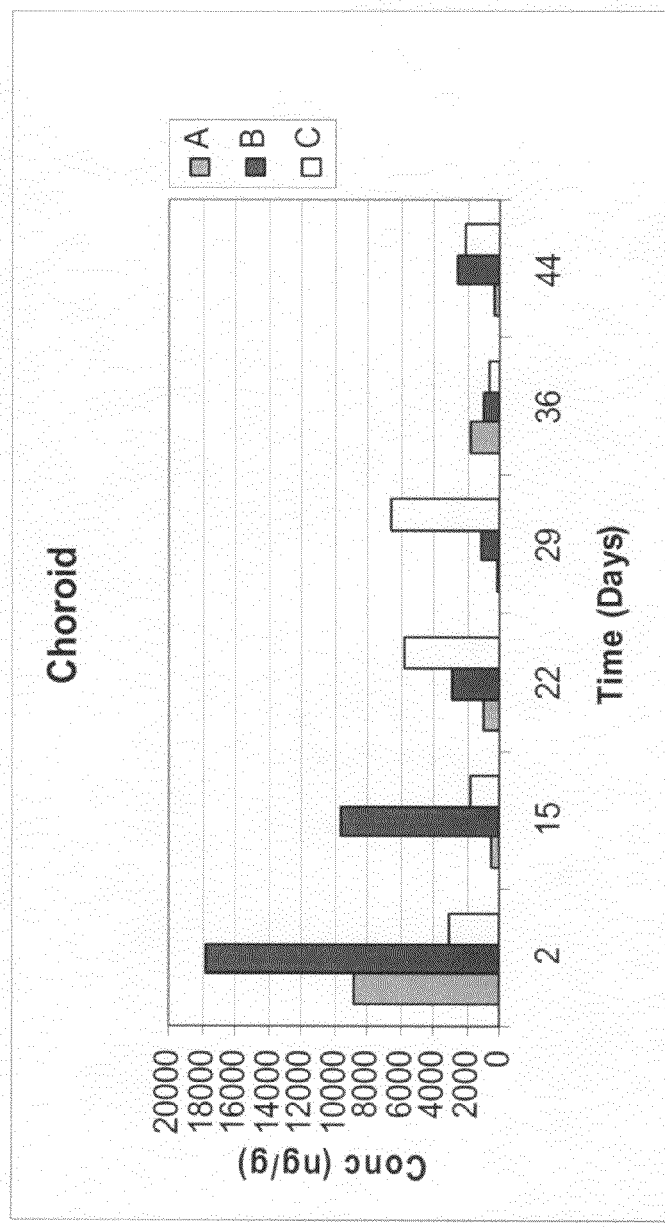
FIGS. 4, 5 and 6 show the distribution of rapamycin in the rabbit choroid, retina and vitreous, respectively, at 2, 15, 22, 29, 36 and 44 days post-intravitreal administration of rapamycin formulations.
Figure 5:
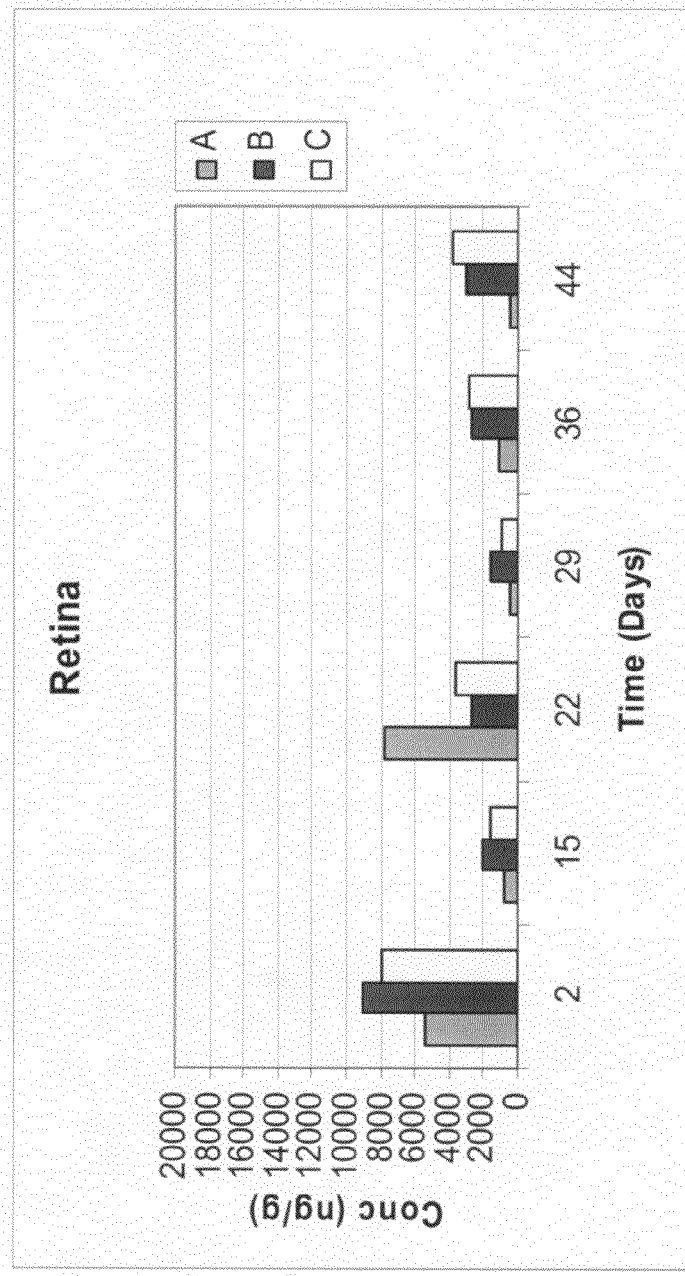
Figure 6:
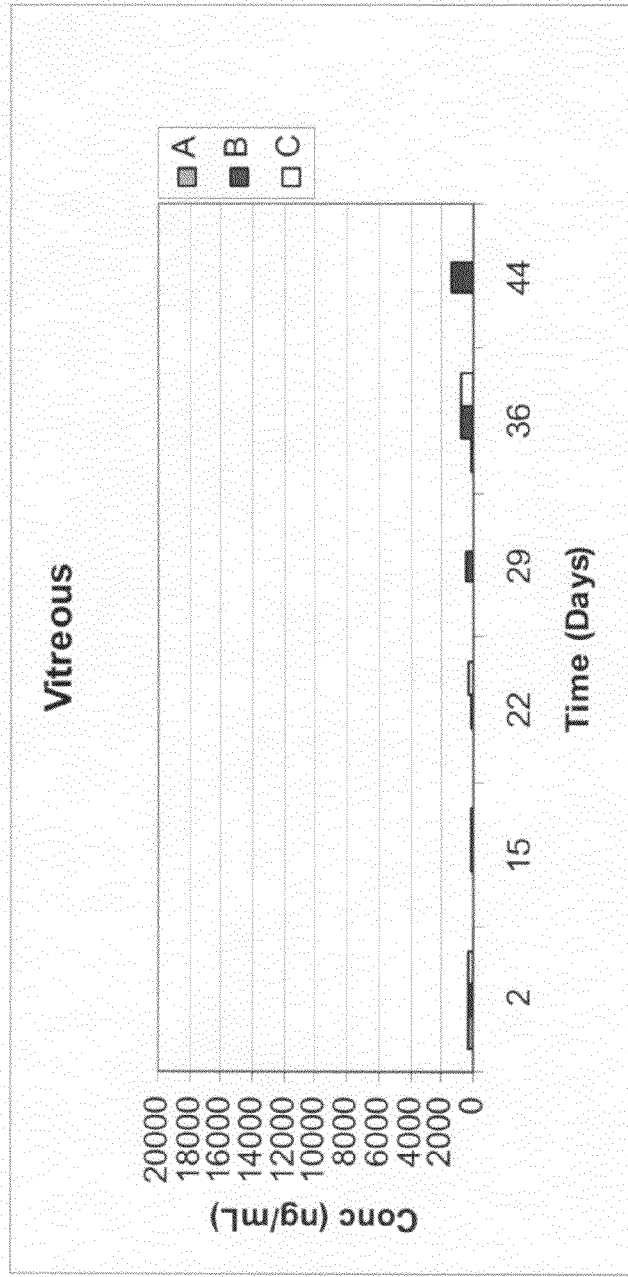

Table 1 and FIGS. 4, 5 and 6 show the distribution of rapamycin in the rabbit choroid, retina and vitreous, respectively, at 2, 15, 22, 29, 36 and 44 days post-dosing. All formulation provided a concentration of rapamycin in the choroid of at least 100 ng/g tissue over a 44 day period.

TABLE 1

Rapamycin Distribution in the Choroid, Retina and Vitreous at Various Timepoints After Intravitreal Injection of 10 μl Rapamycin Atrigel ® Formulations into Rabbit Eyes (expressed in nanograms of rapamycin per gram tissue or mL of vitreous fluid)

| Rapamycin Formulation | Day post-injection | Tissue | | |
|---|---|---|---|---|
| | | Choroid ng/g (SEM)* | Retina ng/g (SEM) | Vitreous ng/mL (SEM) |
| A. 5% (0.5 mg) | 2 | 8735 (5092) | 5329 (1523) | 261 (41) |
| rapamycin in | 15 | 470 (160) | 779 (186) | 72 (10) |
| 95% (50% 65/35 | 22 | 933 (227) | 7767 (7424) | 73 (34) |
| PLGH 0.26 inherent | 29 | 101 (27) | 510 (88) | 30 (25) |
| viscosity and 50% | 36 | 1838 (1797) | 1052 (—) | 114 (97) |
| NNP) | 44 | 331 (113) | 531 (206) | 51 (23) |
| B. 10% (1.0 mg) | 2 | 17765 (7740) | 8990 (5588) | 312 (53) |
| rapamycin in | 15 | 9610 (9706) | 2119 (934) | 200 (49) |
| 90% of (50% 65/35 | 22 | 2932 (1557) | 2625 (472) | 174 (67) |
| PLGH 0.26 inherent | 29 | 1059 (437) | 1601 (322) | 407 (120) |
| viscosity and 50% NNP) | 36 | 962 (604) | 2717 (654) | 727 (604) |
| | 44 | 2529 (2205) | 3073 (1485) | 1452 (1325) |
| C. 10% (1.0 mg) | 2 | 3054 (1810) | 7943 (2279) | 361 (109) |
| rapamycin in | 15 | 1738 (580) | 1608 (47) | 192 (40) |
| 90% of (50% 75/25 | 22 | 5784 (3978) | 3663 (789) | 271 (113) |
| PLGH 13 kD weight | 29 | 6576 (4210) | 1031 (335) | 71 (30) |
| average molecular | 36 | 681 (267) | 2894 (674) | 760 (797) |
| weight and 50% NNP) | 44 | 2083 (896) | 3783 (1185) | 52 (10) |

*SEM: Standard Error of the Mean

Ophthalmic examinations were conducted at each time point on the eyes. The results of the examinations are tabulated below in Table 2.

TABLE 2

| | 5%/65/35 PLGH 0.26 InV | 10%/65/35 PLGH 0.26 InV | 10%/75/25 PLGH 13 kDa | 10%/85/15 PLGH 25 kDa | 10%/85/15 PLG 25 kDa |
|---|---|---|---|---|---|
| Conjunctival Irritations | Minimal to mild | Mild | Mild | Mild, chronic | Mild, chronic |
| Anterior Chamber Inflammation | Minimal to mild | Mild to moderate | Mild | Mild to moderate | Mild to moderate |

TABLE 2-continued

|  | 5%/65/35 PLGH 0.26 InV | 10%/65/35 PLGH 0.26 InV | 10%/75/25 PLGH 13 kDa | 10%/85/15 PLGH 25 kDa | 10%/85/15 PLG 25 kDa |
|---|---|---|---|---|---|
| Cataract | None | None | 2/24 eyes | None | None |
| Posterior Segment Involvement | Minimal to mild | Mild | Mild | Mild to moderate | Mild to moderate |
| Movement of the Implant | 5/20 by Day 22, all by Day 44 | 1/20 by Day 22, all by Day 44 | None by Day 22, all by Day 44 | None by Day 22, all by Day 44 | None by Day 22, all by Day 44 |
| Intraocular Pressure | Normal | Normal | Normal | Normal | Normal |

The rapamycin/ATRIGEL® formulations displayed varying degrees of anterior and/or posterior irritations, with greater irritation generally correlating with increases in drug dose. 5% rapamycin loading is considered to be a well tolerated dose for the 1-month intravitreal formulation. Migration/displacement of implants was occasionally observed, but would not likely impair vision due to the small size of the implants. Control ATRIGEL® formulations lacking rapamycin exhibited similar conjunctival irritations, but minimal or no anterior chamber or posterior segment irritations by Day 29. Most implants containing control ATRIGEL® formulations moved by Day 22.

Histopathology was conducted at Day 29 post-dosing on eyes injected with 10 µL of the formulations described above. Results of the histopathology are tabulated below in Table 3.

TABLE 3

|  | 5%/65/35 PLGH 0.26 InV (4 eyes) | 10%/65/35 PLGH 0.26 InV (4 eyes) | 10%/75/25 PLGH 13 kDa (4 eyes) | 10%/85/15 PLGH 25 kDa (4 eyes) | 10%/85/15 PLG 25 kDa (4 eyes) |
|---|---|---|---|---|---|
| Conjunctiva, episclera irritations | Normal | Normal | Normal | Normal | Minimal to mild, prevalent |
| Anterior Chamber irritation | Normal | Normal | Minimal to mild | Minimal to mild | Mild to moderate, prevalent |
| Cataract | Normal | Mild | Minimal | Minimal | Mild to moderate, prevalent |
| Posterior Segment involvement | Normal | Mild | Minimal to moderate | Minimal to mild | Minimal and prevalent |
| Periocular muscles | Normal | Normal | Normal | Normal | Normal |
| Injection site irritations | Minimal | Mild | Mild | Minimal | Mild |

Formulation I (5% Rapamycin in 50% 65/35 PLGH 0.26 InV and 50% NMP) is a well-tolerated formulation, based on both ocular examination and histopathology. Control 65/35 PLGH and 75/25 PLGH ATRIGEL® formulations lacking rapamycin showed minimal changes at the injection site. Blank 85/15 PLG and PLGH ATRIGEL® formulations exhibited mild to moderate irritations in the anterior and posterior segment of the eye.

Figure 7:
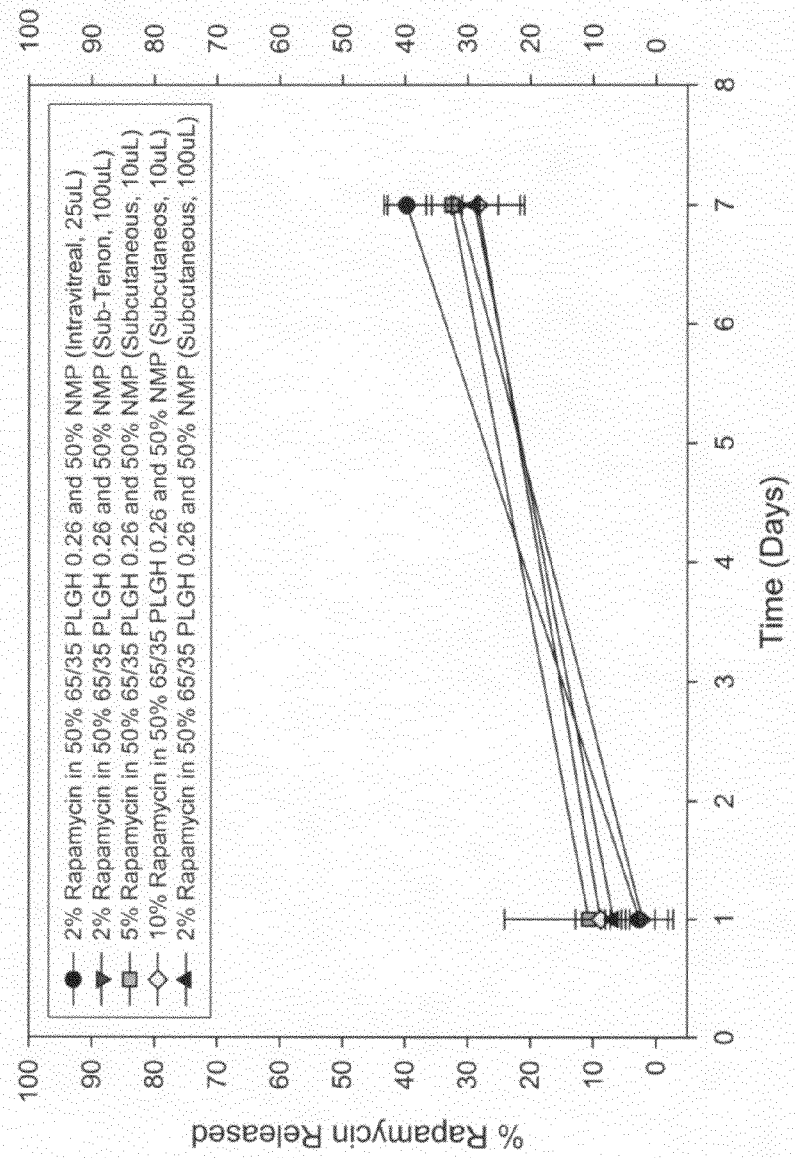
FIG. 7 is a graphical comparison of the release of rapamycin from various formulations injected into intravitreal, subtenon and subcutaneous regions. Release of rapamycin is very similar between each of the formulations and routes of administration.

FIG. 7 is a graphical representation of the release of rapamycin from various formulations injected into intravitreal, sub-tenon and subcutaneous regions. The intravitreal and sub-tenon injections into rabbits and subcutaneous injections into rats (essentially described in the above examples) were analyzed at days 1 and 7. Implants were extracted and HPLC was conducted as described above. The data suggests that the release rate of rapamycin from ATRIGEL® implants is very similar when comparing subcutaneous routes to intravitreal and sub-tenon injection routes. Screening of various ocular formulations is thus feasible using the subcutaneous route of administration.

Example 4

Subcutaneous Injection of ATRIGEL®/Rapamycin Formulations

Materials and Methods

In this 24-hour study, ten ATRIGEL® formulations were tested in fifty male Sprague Dawley Rats (five animals per treatment group). On Day 0, while under general isoflurane anesthesia, each rat was placed in sternal recumbency, its DT region shaved, and the injection site wiped with isopropanol. Each animal was administered a single 100 µL subcutaneous injection of appropriate test article in the dorsal thoracic region. At approximately 24 hours, the rats were euthanized with $CO_2$. Test sites were dissected and evaluated for macroscopic tissue reactions immediately following euthanasia. Implants were removed and HPLC conducted as in Example 1. Representative photographs were taken of the test sites and implants. Injection sites were evaluated on Days 0 and 1 for any abnormalities including redness, bleeding, swelling, discharge, bruising, and test article extrusion. Additionally, animals were observed post-administration for signs of overt toxicity.

Preparation of ATRIGEL® Polymer Solutions

Five grams of polymer stock solutions were prepared by weighing a known amount of each polymer solid into individual 20 mL scintillation vials. A known amount of N-methyl-2-pyrrolidone (NMP) was added to each polymer and the mixture placed on a jar mill. The vials were mixed at least 24 hours to create a visually clear solution. Following dissolution of the polymer the vials were sterilized by gamma irradiation at 19.8-22.6 kGy.

Preparation of Rapamycin/ATRIGEL® Formulations

The preparation of the A/B syringe configuration was done as follows: to 1.2 mL female syringes approximately 980 mg of sterilized ATRIGEL® polymer solutions was added. Then, in 1.2 mL male syringes, approximately 20 mg of rapamycin was weighed. Prior to injection the two syringes were coupled and mixed 90 cycles to afford the 2.0 weight % formulation.

| Test Article Identification | |
|---|---|
| Group | Formulation |
| I | 2% rapamycin in 50% 85/15 PLGH (InV 0.27), and 50% NMP |
| II | 2% rapamycin in 50% 85/15 PLG (InV 0.28), and 50% NMP |
| III | 2% rapamycin in 50% 75/25 PLGH (InV 0.24), and 50% NMP |
| IV | 2% rapamycin in 50% 75/25 PLG (InV 0.28), and 50% NMP |
| V | 2% rapamycin in 40% 85/15 PLG (InV 0.35), and 60% NMP |
| VI | 2% rapamycin in 40% 75/25 PLG (InV 0.35), and 60% NMP |
| VII | 2% rapamycin in 48% 75/25 PLGH (InV 0.24), 2% PEG5000 - 70/30 PLG (InV 0.79), and 50% NMP |
| VIII | 2% rapamycin in 48% 75/25 PLG (InV 0.28), 2% PEG5000 - 70/30 PLG (InV 0.79), and 50% NMP |
| IX | 2% rapamycin in 48% 85/15 PLGH (InV 0.27), 2% PEG5000 - 70/30 PLG (InV 0.79), and 50% NMP |
| X | 2% rapamycin in 48% 85/15 PLG (InV 0.28), 2% PEG5000 - 70/30 PLG (InV 0.79), and 50% NM |

NOTE:
All percentages are weight to weight (w/w) and all inherent viscosities (InV) are in units of dL/g.

| Manufacturer Information | | |
|---|---|---|
| Substance | Manufacturer | Lot # |
| 85/15 PLGH 0.27 | QLT USA | 1654-66 |
| 85/15 PLG 0.28 | APT | TN080702-002 |
| 75/25 PLGH 0.24 | Alkermes | 00-141-150 |
| 75/25 PLG 0.28 | BPI | D99095 |
| 85/15 PLG 0.35 | BPI | D95002 |
| 75/25 PLG 0.35 | QLT USA | 1799-12 |
| PEG5000-70/30 PLG 0.79 | BPI | D97132 |
| NMP | Intl. Specialty Prod. | TN102804-011 |
| Rapamycin | Molcon Corp. | RDC-04367 |

Results

The targeted dose in this study was 100 mg (100 µL) of formulation. The mean injection weights with standard deviation, for Groups I through X, respectively, are as follows: 100.36±11.88 mg, 104.14±19.53 mg, 119.82±12.86 mg, 111.48±38.92 mg, 120.08±44.54 mg, 113.16±20.37 mg, 99.72±21.87 mg, 101.36±22.38 mg, 119.42±9.13 mg, and 109.66±15.75 mg. After extraction, all implants were firm and non-fragmenting.

Example 5

Effects of Intravitreal Rapamycin on Choroidal Neovascularization

Pharmacology studies were performed to investigate the effects of intravitreally delivered rapamycin on the development of choroidal neovascularization. The studies also aimed at determining the relationship between ocular tissue concentrations after intravitreal injection and the pharmacodynamic and pharmacologic effects of rapamycin.

Materials and Methods

Induction of CNV

Thermal laser infrared light (diode laser 810 nm) at 200 mW for 0.075 seconds was delivered to the fundus of Long Evans rats using a slit lamp and a slit lamp adaptor. A total of 6 lesions with 75 µm diameter were placed in a circular pattern surrounding the optic disc on the posterior pole.

Intravitreal Administration

Intravitreal injection was performed immediately after laser photocoagulation. Briefly, three days prior to the injection, 0.3% Ciloxan ointment was applied to the eye once daily. At the time of injection, the eye pocket was irrigated and the conjunctiva swabbed with 1.0% Betadine solution. A 30-gauge needle connected to a 10-µL Hamilton syringe that contained 5 µL carboxymethylcellulose (CMC)-based Rapamycin suspension (0.5, 5, 10 or 40 mg/mL) or CMC vehicle alone was inserted 1 mm posterior to the corneoscleral limbus. The injection began when the bevel of the needle faced down and reached the vitreous about 1-2 mm in depth with the visual aid of a dissecting microscope. After injection, topical 0.3% Ciloxan ointment was applied to the eye once daily for 2 days.

Fluorescein Angiography (FA) Evaluation of CNV

FA was performed on the 14th day after intravitreal injection of Rapamycin. Briefly, a 25-gauge butterfly catheter was placed in the tail vein on an anesthetized animal and a Heparin-Lock solution (0.50 mL of 10,000 IU/mL Heparin Sodium with 0.95 mL 0.9% Saline) was used to fill the catheter line to maintain intravenous access. A dose of 10 mg/kg of Diofluor 10% (Fluorescein Sodium 10%) was delivered through the tail vein, followed by a flush of sterile saline to ensure full delivery of Diofluor 10%. An infusion pump (Becton-Dickinson) connected to a 60 cc syringe was used to infuse the Diofluor 10% at a constant rate of 6 mL/min (8.4-13.2 pounds per square inches) to allow for consistency in the synchronization of the fluorescein bolus injection and the angiogram acquisition. Photographs were taken with a fluorescence fundus camera at 1-10, 30, 60, 90, 180, and 300 sec after Diofluor 10% administration. The leakiness of CNV was assessed by two independent readers masked to the treatment.

Histological Evaluation of CNV

Eyes were enucleated and chorioretinal tissues that contained the CNV lesions prepared and fixed for about 18 hours in formic acid alcohol, and then replaced with 70% alcohol until the specimen was processed to wax by a standard method. Slides were stained with mouse anti rat CD31 (Chemicon, UK) by a standard immunohistochemistry protocol. This briefly consisted of removal of endogenous peroxidase enzymes with methanol and hydrogen peroxide, primary antibody as above, and the secondary donkey antibody anti mouse conjugated to biotin. Streptavidin ABC and Vector VIP substrate (Vector labs, Burlingame Calif.) were further added. Haematoxylin was used as a counterstain. Representative images before and after the center of each CNV lesion were taken using the 20× objective of an Olympus BX61 microscope fitted with a Spot RT colour camera (Diagnostic instruments, MI USA). Each image was applied to the standard image analysis macro in the software Image pro to identify the mean of lesion area for each CNV and the mean of CD31 positive cell counts (i.e. endothelial cells) within the CNV lesion area. All measurements were generated by two independent readers masked to the treatments. The data was analyzed in Excel and GraphPad Prism. The 80% correlation found between readers was deemed acceptable.

Pharmacodynamic Evaluation

Upon euthanasia of the animal, the eyes were cut along the equator, separating the anterior and posterior segments. The vitreous was removed and the remaining back of eye (with intact retina, choroid and sclera) was placed in a labeled Nalgene Cryotube, immediately immersed in liquid nitrogen, and stored at −80° C. until ready to use. Upon lysis, tubes containing tissue were brought to room temperature to thaw. Tissues were lysed in 400 μL of lysis buffer (Cell Signaling CAT #: 9803) with protease inhibitor cocktail (Calbiochem CAT #: 539131) and beads in Matrix D Tubes (Q-biogene, CAT #: 6913-100) in the Fast Prep Instrument. Protein concentration of each sample was determined using the Pierce BCA Protein Determination Kit (Pierce, CAT #: 23225) and BSA as a standard. Samples were analyzed by SDS-PAGE, followed by western blotting. Primary antibodies included antibodies against phosphorylated S6 ribosomal protein, S6 ribosomal protein, and beta-actin antibody. Secondary antibodies included goat anti-Rabbit HRP linked antibodies, or Goat anti-Mouse HRP linked antibodies. Bound antibodies were detected using ECL or ECL plus Western Blotting Reagents. Densitometric evaluation was performed on blots scanned by Bio-Rad Multi-Analyst Software, and analyzed in MS Excel and GraphPad Prism.

Results

Rapamycin Inhibited the Development of CNV

Figure 8:
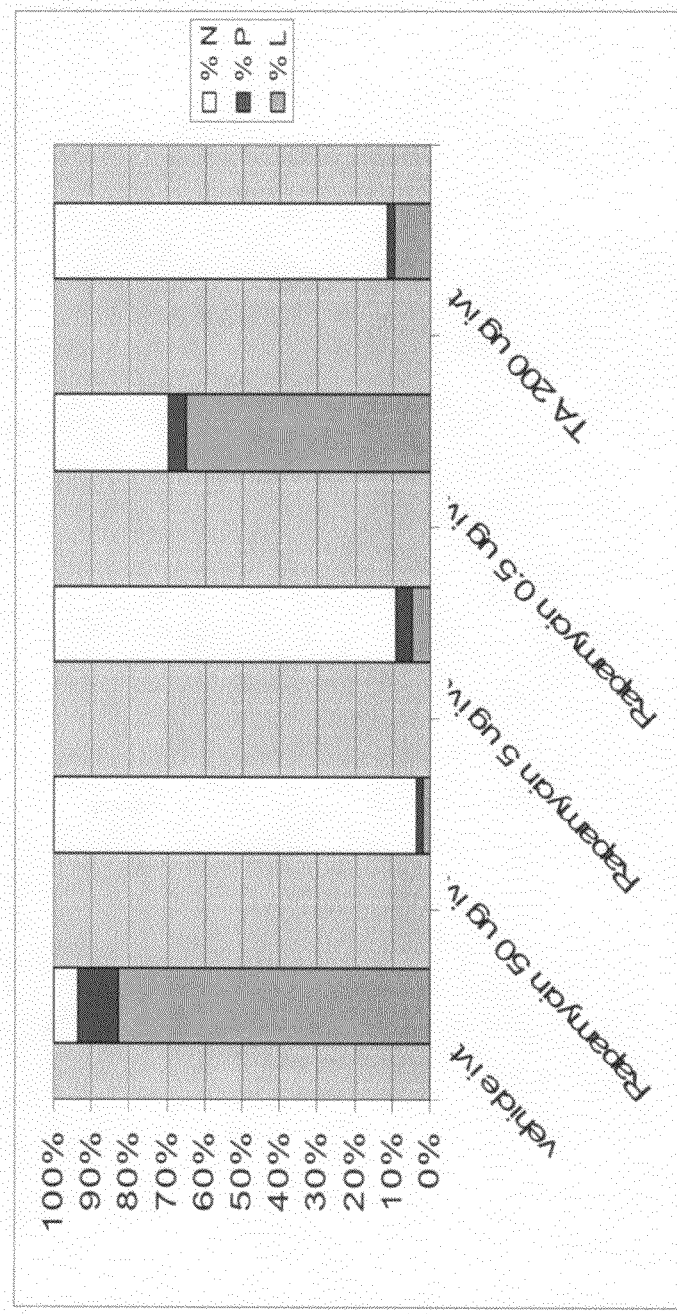
FIG. 8 is an angiographical evaluation of the effect of rapamycin on the development of choroidal neovascularization (CNV) in a laser-induced CNV rat model. Rapamycin inhibited the development of CNV. N=non-leaky CNV lesion; L=leaky CNV lesion; P=partial leaky CNV lesion.

A dose dependent inhibition of CNV development was observed for the carboxymethylcellulose (CMC) based rapamycin formulation that was intravitreally injected immediately after laser photocoagulation. As shown in FIG. 8, the incidence of developing leaky CNV 2 weeks after laser photocoagulation was 83% for the CMC vehicle control, whereas it was reduced to 2%, 5% and 65% when a single intravitreal injection of 50 μg, 5 μg and 0.5 μg rapamycin in CMC, respectively. A positive control for this model, triamcinolone acetonide (TA) at an intravitreal dose of 200 μg also prevented CNV development and showed a 10% incidence of leaky CNV at the 14-day follow-up.

Figure 9:
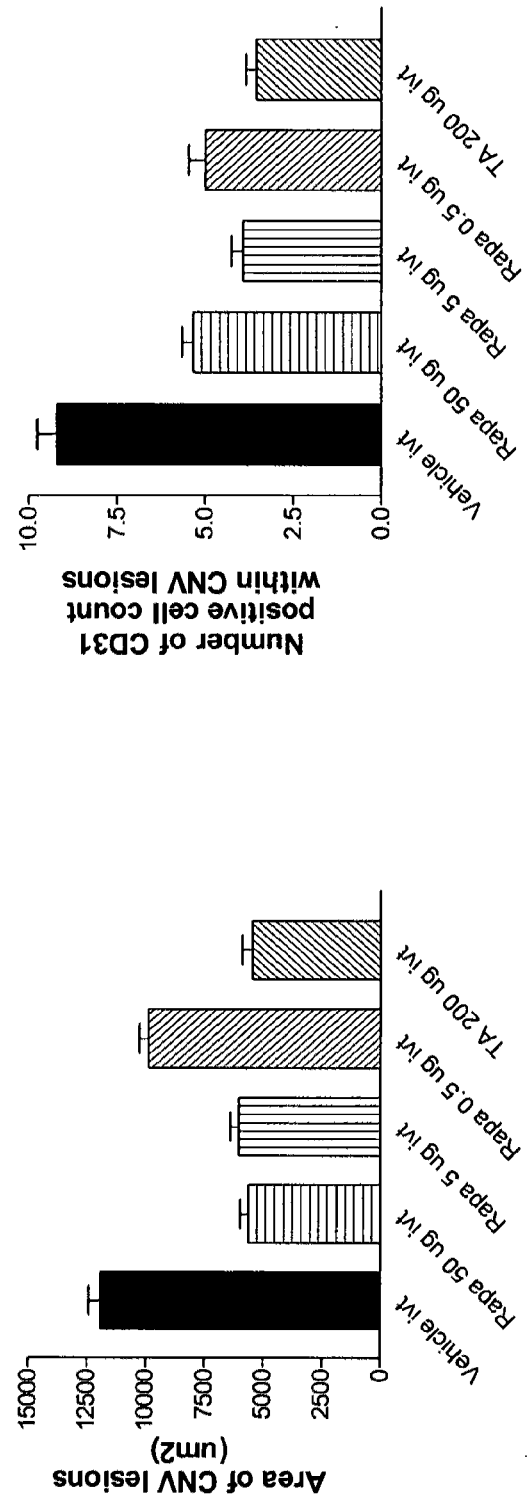
FIG. 9 illustrates the effect of rapamycin on the CNV area and CD31-positive cell count within the CNV area in the laser-induced CNV model. The top graph shows that the CNV area was reduced after rapamycin treatment in a dose-dependent manner; the bottom graph shows the same dose-dependent effect on the number of endothelial cells in the CNV lesions.

In agreement with angiographic results, CNV area and the number of endothelial cells in the CNV lesions were reduced after rapamycin treatments in a dose-dependent manner (FIG. 9). Rapamycin intravitreally given at 50 μg, 5 μg and 0.5 μg caused a 50%, 55% and 15% reduction in CNV area, respectively, and an overall 50-60% reduction in the number of endothelial cells within the CNV area, compared to the vehicle group. Similar to rapamycin, TA also inhibited CNV area and endothelial cell count by approximately 50% and 60%.

Pharmacodynamic Evaluation of Intravitreally Administered Rapamycin

Figure 10:
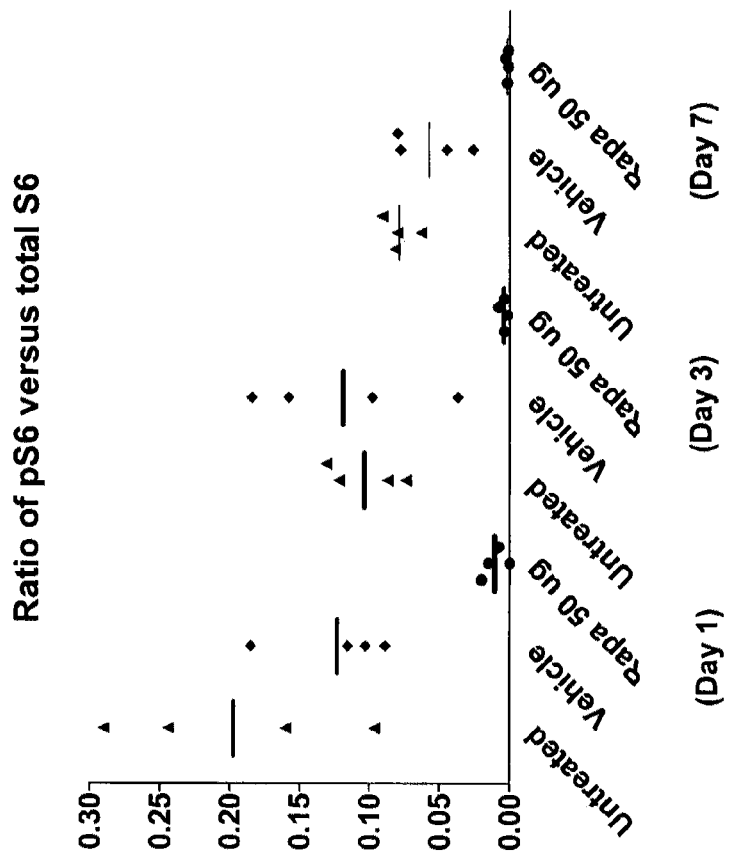
FIG. 10 shows the effects of intravitreally administered rapamycin on serine phosphorylation of S6 ribosomal protein extracted for chorioretinal tissues at day 1 (first 3 columns), day 3 (second three columns) and day 7 (last three columns) post-dosing. The level of phosphorylated Ser235/236 on S6 ribosomal protein was significantly reduced in the rapamycin treated eyes compared to the untreated or vehicle-injected eyes.

Rapamycin inhibits mTOR activity, which then downregulates Ser235/236 phosphorylation of the downstream target of mTOR, the S6 ribosomal protein. In order to evaluate the pharmacodynamic response of intravitreally administered rapamycin in the eye, the serine phosphorylation of S6 protein extracted from chorioretinal tissues was analyzed by western blot, and standardized by the total amount of S6 protein. As illustrated in FIG. 10, the level of phosphorylated Ser235/236 on S6 ribosomal protein was significantly reduced in the rapamycin treated eyes, in contrast to the untreated eyes or the vehicle injected eyes. The inhibitory effect of rapamycin on S6 phosphorylation occurred within the first 24 h and lasted for 7 days post-dosing, the longest follow-up timepoint.

Conclusions

Rapamycin is a potent inhibitor of CNV. In a rat model of laser-induced CNV, rapamycin suppressed the activation of its target mTOR at all tested time points. A dose of 5 μg intravitreally injected evoked nearly a complete response in the rat model.

Example 6

Safety Studies on Atrigel®

Experiments were conducted to determine the safety of the flowable compositions as described herein, but with no rapamycin.

Materials and Methods

Various ATRIGEL® formulations in NMP with no rapamycin were administered by intravitreal injection and injection into, the posterior subtenon (episcleral) region of New Zealand white and Dutch Belted rabbits. A curved blunt cannula facilitated the precision and ease of dosing for subtenon injections. Between 10 and 50 μL were injected intravitreally, while between 50 and 200 μL were used for subtenon injection. After periods of time ranging from 24 hours to 3 months post-dosing, ophthalmic examination, intraocular pressure, and histopathology assessments were conducted.

Results

Eyes that received intravitreal injections showed no significant adverse events up to 3 months post-dosing. Ten microliters was determined to be an optimal volume for intravitreal injection. The shape of the implant was controlled by the composition and the speed of injection. No significant safety concerns were evident upon histopathological examination with up to 25 μL ATRIGEL® alone.

Eyes that received subtenon injections were given ophthalmic examinations. Acute mild conjunctival irritations occurred at Day 1 post-dosing, but were usually resolved by Day 3-7. No other adverse effects were evident up to 3 months.

Histopathology was also conducted on eyes that received subtenon injections. Inflammatory and granulation tissue reactions to the ATRIGEL® implant occurred at all volumes tested. These findings are typical of a foreign body reaction. Minimal to moderate muscle necrosis was seen at 7 days, and up to Day 29. This necrosis appeared to be a secondary effect of the implant being adjacent to muscle fibers (by-stander effect). Use of smaller injection volumes is preferred.

Example 7

25% Rapamycin Formulations

Rapaymcin formulations were prepared as in Example 1, with the following components:
I: 25% rapamycin in 50% 65/35 PLGH 0.26 inherent viscosity and 50% NMP
II. 25% rapamycin in 50% 65/35 PLGH 0.26 inherent viscosity and 50% NMP with 0.2% hydroxproply methylcellulose (Methocel®, Dow Chemical)

It was observed that the addition of Methocel to the rapamycin solution facilitated wetting of the powder. Test samples of dissolved rapamycin with and without Methocel were lyophilized. It was observed that samples containing Methocel lyophilized as a cake-like substance. Samples without Methocel tended to form a loose fluffy powder. It is believed that for scale up manufacturing, the addition of a small amount (0.1 to 0.5%) of hydroxpropyl cellulose or other cellulose derivative will prevent the migration of lyphilized rapamycin out of syringes. The addition of Methocel did not impact the release of rapamycin from the Atrigel formulations of the invention.

Example 8

IC50 of Rapamycin

Targeted tissue concentrations were estimated from in vitro experiments assessing the inhibitory effects of rapamycin on endothelial cell proliferation and cytokine release from immune cells. Human umbilical endothelial cells were activated with Vascular Endothelial Growth Factor (VEGF) and incubated with various concentrations of rapamycin. Cell proliferation was evaluated by quantifying $^3$H-thymidine incorporation after 48 hours. In this model, the concentration that inhibited endothelial cells proliferation by 50% (IC50) was 69 nM. The IC50 for the release of TNFalpha from Lipopolysaccharide and IFNgamma treated THP-1 cells (monocytic cell line) was ~1 nM and the IC50 for the release of IFNgamma from human peripheral blood T cells stimulated with phytohemagglutanin was ~2 nM.

Based on the IC50 results, concentrations of rapamycin in target tissue that are in excess of 100 ng/gram of tissue should provide a therapeutic effect.

REFERENCES

1. Janus, A. et al: The Mammalian Target of the Rapamycin (mTOR) Kinase Pathway Its Role in Tumourigenesis and Targeted Antitumour Therapy. Cellular & Molecular Biology Letters 10 (3), 479-498 (2005).
2. Jungbauer, F. H. W. et al: Toxic hygroscopic contact reaction to N-methyl-2-pyrrolidone. Contact Dermatitis 45, 303-304 (2001).
3. Leira, H. L. et al: Irritant cutaneous reactions to N-methyl-2-pyrrolidone (NMP). Contact Dermatitis 27, 148-150 (1992).

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

What is claimed is:

1. An implant formed in situ comprising:
   (a) a biocompatible, biodegradable, substantially water insoluble thermoplastic polymer and
   (b) rapamycin or a rapamycin derivative;
   wherein the implant has a solid monolithic structure, wherein the implant is located in the intravitreal region of a mammal, affixed to the sclera of the eye, wherein the implant has a microporous matrix, the matrix being a core surrounded by a skin, wherein the core and skin are composed of the biocompatible, biodegradable, substantially water insoluble thermoplastic polymer and wherein the implant is surrounded by body tissue.

2. An implant precursor formed in situ comprising:
   (a) a biodegradable, biocompatible thermoplastic polymer that is at least substantially insoluble in aqueous medium, water or body fluid;
   (b) a biocompatible organic liquid in which the thermoplastic polymer is soluble; and
   (c) rapamycin or a rapamycin derivative;
   wherein the biocompatible organic liquid is N-methyl-2-pyrrolidone, 2-pyrrolidone, N, N-dimethylformamide, dimethyl sulfoxide, propylene carbonate, caprolactam, triacetin, or any combination thereof; wherein the implant precursor is located in the intravitreal region of a mammal, affixed to the sclera of the eye, and the implant precursor has a solid or gelatinous microporous matrix, the matrix being a core surrounded by a skin, wherein the core and skin are composed of the biodegradable, biocompatible thermoplastic polymer and wherein the implant precursor is surrounded by body tissue.

3. The implant or implant precursor of claim 1 or 2 wherein the thermoplastic polymer comprises at least one polyester.

4. The implant or implant precursor of claim 1 or 2 wherein the thermoplastic polymer is a linear or branched polymer.

5. The implant or implant precursor of claim 4 wherein the thermoplastic polymer is a poly(DL-lactide-co-glycolide) having a carboxy terminal group.

6. The implant or implant precursor of claim 3 wherein the thermoplastic polyester is a 50/50, 55/45, 65/35, 75/25, 85/15, 90/10, or 95/5 poly(DL-lactide-co-glycolide).

7. The implant or implant precursor of claim 1 or 2 wherein the thermoplastic polymer is a polyester of one or more hydroxy carboxylic acids, or is a polyester of a combination of one or more diols and one or more dicarboxylic acids.

8. The implant or implant precursor of claim 7 wherein the hydroxy carboxylic acid or acids are in the form of dimers.

9. The implant or implant precursor of claim 7 wherein the thermoplastic polyester is present in about 20 wt. % to about 90 wt. %, or about 30 wt. % to about 70 wt. % of the composition, and optionally the thermoplastic polyester has an average molecular weight of from about 15,000 to about 45,000 Daltons.

10. The implant precursor of claim 2 wherein the biocompatible organic liquid has a solubility in aqueous medium or body fluid ranging from insoluble to completely soluble in all proportions.

11. The implant precursor of claim 2 wherein the biocompatible polar aprotic organic liquid is N-methyl-2-pyrrolidone.

12. The implant precursor of claim 2 wherein the biocompatible organic liquid is present in about 10 wt. % to about 90 wt. % of the implant precursor, or the biocompatible organic liquid is present in about 30 wt. % to about 70 wt. % of the implant precursor.

13. The implant or implant precursor of claim 1 or 2 wherein the rapamycin or rapamycin derivative is present in about 0.001 wt. % to about 30 wt. % of the implant or implant precursor, or the rapamycin or rapamycin derivative is present in about 1 wt. % to about 25 wt. % of the implant or implant precursor.

14. The implant precursor of claim 2 wherein the rapamycin or rapamycin derivative is present in about 5% of the composition, the biocompatible organic liquid is NMP present in about 50 wt. % of the composition, and the thermoplastic polymer is a 65/35 poly(DL-lactide-co-glycolide).

15. The implant or implant precursor of claim 1 or 2 wherein the implant or implant precursor has a volume of about 0.001 mL to about 0.2 mL.

16. The implant or implant precursor of claim 1 or 2 wherein the rapamycin or rapamycin derivative is in the form of a salt and the salt gegenion is derived from a pharmaceutically acceptable organic or inorganic acid.

17. The implant or implant precursor of claim 16 wherein the gegenion is a polycarboxylic acid.

18. The implant of claim 1 having a substantially linear cumulative release profile.

19. The solid implant of claim 1 wherein the core contains pores of diameters from about 1 to about 1000 microns, and optionally the skin contains pores of smaller diameters than those of the core pores, and optionally the skin pores are of a size such that the skin is functionally non-porous in comparison with the core.

* * * * *

UNITED STATES PATENT AND TRADEMARK OFFICE
CERTIFICATE OF CORRECTION

PATENT NO. : 8,313,763 B2
APPLICATION NO. : 11/706569
DATED : November 20, 2012
INVENTOR(S) : Margaron et al.

It is certified that error appears in the above-identified patent and that said Letters Patent is hereby corrected as shown below:

On the Title Page:

On page 2, in column 2, under "Other Publications", line 9, after "11/244,438", insert --,--, therefor On page 2, in column 2, under "Other Publications", line 9, delete "2010"", and insert --2010", 7 pgs.--, therefor On page 2, in column 2, under "Other Publications", line 12, after "2010", delete ",", therefor On page 2, in column 2, under "Other Publications", line 23, delete "2001),303-304" and insert --2001), 303-304--, therefor On page 2, in column 2, under "Other Publications", line 25, delete "(1992),148-150" and insert --(1992), 148-150--, therefor On page 2, in column 2, under "Other Publications", line 38, delete ""European Office Action Jan. 18, 2012"." and insert --"European Application Serial No. 08725587.3, Office Action mailed Jan. 18, 2012", 5 pgs.--, therefor In the Claims:

In column 46, line 53, in Claim 11, after "biocompatible", delete "polar aprotic", therefor Signed and Sealed this
Thirtieth Day of April, 2013

Teresa Stanek Rea
*Acting Director of the United States Patent and Trademark Office*